(12) United States Patent
Entabi

(10) Patent No.: US 10,004,533 B2
(45) Date of Patent: Jun. 26, 2018

(54) SURGICAL TOOLS AND SYSTEM FOR SAFELY ACCESSING BODY CAVITIES AND METHODS OF USING THE SAME

(71) Applicant: Fateh Entabi, Visalia, CA (US)

(72) Inventor: Fateh Entabi, Visalia, CA (US)

(*) Notice: Subject to any disclaimer, the term of this patent is extended or adjusted under 35 U.S.C. 154(b) by 451 days.

(21) Appl. No.: 14/660,954

(22) Filed: Mar. 18, 2015

(65) Prior Publication Data

US 2016/0089180 A1 Mar. 31, 2016

Related U.S. Application Data

(60) Provisional application No. 62/057,978, filed on Sep. 30, 2014.

(51) Int. Cl.
*A61B 17/34* (2006.01)
*A61M 25/00* (2006.01)
(Continued)

(52) U.S. Cl.
CPC ...... *A61B 17/3415* (2013.01); *A61B 17/3474* (2013.01); *A61B 17/3496* (2013.01);
(Continued)

(58) Field of Classification Search
CPC ............ A61B 17/3415; A61B 17/3474; A61B 17/3496
See application file for complete search history.

(56) References Cited

U.S. PATENT DOCUMENTS 2,623,521 A 12/1952 Shaw
3,993,079 A * 11/1976 Henriques de Gatztanondo ....... A61B 17/3417
604/164.01
(Continued)

FOREIGN PATENT DOCUMENTS

CN 201290952 8/2009
EP 0821603 2/1998
(Continued)

OTHER PUBLICATIONS

Tan et al., Flexible transbronchial optical frequency domain imaging smart needle for biopsy guidance, Biomedical Optics Express, Aug. 1, 2012, vol. 3, No. 8, (published Jul. 27, 2012).
(Continued)

*Primary Examiner* — Quynh-Nhu H Vu
(74) *Attorney, Agent, or Firm* — William K. Nelson; Mark D. Miller

(57) ABSTRACT

The application discloses a set of surgical instruments that may be used to access a human or animal body cavity for medical purposes without causing damage to internal tissues or organs therein, and methods of using the same. The instruments include a safety needle and flexible sheath that may be coupled together and used to establish a minimally invasive method to access a targeted body cavity while preventing or reducing damage to organs or tissues within the targeted cavity. Additional instruments are included within the invention that may be used to establish an access port in the wall of the targeted cavity. That port may be used to introduce catheters or other instruments into the body cavity. It may also be used as a drainage tube for draining or injecting gases and/or fluids from or into the targeted cavity.

19 Claims, 24 Drawing Sheets

(51) Int. Cl.
*A61M 27/00* (2006.01)
*A61M 25/06* (2006.01)
*A61B 90/00* (2016.01)

(52) U.S. Cl.
CPC .............. *A61B 2090/0807* (2016.02); *A61B 2090/3937* (2016.02)

(56) References Cited

U.S. PATENT DOCUMENTS

| | | | |
|---|---|---|---|
| 4,487,209 A | | 12/1984 | Mehl |
| 4,573,448 A | * | 3/1986 | Kambin ............. A61B 17/3417 |
| | | | 128/898 |
| 4,907,598 A | | 3/1990 | Bauer |
| 5,059,183 A | * | 10/1991 | Semrad ................. A61M 25/06 |
| | | | 604/158 |
| 5,098,388 A | | 3/1992 | Kulkashi et al. |
| 5,121,751 A | | 6/1992 | Panalletta |
| 5,370,675 A | | 12/1994 | Edwards et al. |
| 5,423,760 A | * | 6/1995 | Yoon ................. A61B 17/3417 |
| | | | 604/158 |
| 5,601,588 A | | 2/1997 | Tonomura et al. |
| 5,669,883 A | | 9/1997 | Scarfone et al. |
| 5,697,911 A | * | 12/1997 | Yarger ............. A61B 17/00234 |
| | | | 604/158 |
| 5,772,678 A | * | 6/1998 | Thomason ......... A61B 17/3417 |
| | | | 604/164.1 |
| 5,997,486 A | * | 12/1999 | Burek ................ A61B 10/0045 |
| | | | 600/573 |
| 6,217,556 B1 | | 4/2001 | Ellingson et al. |
| 6,273,874 B1 | | 8/2001 | Parris |
| 6,443,910 B1 | * | 9/2002 | Krueger ............... A61B 10/025 |
| | | | 600/567 |
| 6,770,079 B2 | * | 8/2004 | Bhatnagar .......... A61B 17/3472 |
| | | | 606/86 R |
| 7,022,109 B1 | | 4/2006 | Ditto |
| 7,169,114 B2 | | 1/2007 | Krause |
| 8,021,338 B2 | | 9/2011 | Adams |
| 8,192,402 B2 | * | 6/2012 | Anderson .......... A61B 17/3415 |
| | | | 604/164.1 |
| 8,512,368 B2 | | 8/2013 | Sato et al. |
| 8,551,051 B2 | | 10/2013 | Salto et al. |
| 2007/0016141 A1 | | 1/2007 | Salto et al. |
| 2010/0274081 A1 | | 10/2010 | Okoniewski |
| 2012/0296255 A1 | * | 11/2012 | Feng ................. A61M 25/0612 |
| | | | 604/8 |
| 2013/0131501 A1 | | 5/2013 | Blaivas et al. |
| 2013/0131502 A1 | | 5/2013 | Blaivas et al. |
| 2013/0158427 A1 | * | 6/2013 | Choi .................. A61B 17/3415 |
| | | | 600/554 |
| 2013/0310750 A1 | | 11/2013 | Hopman et al. |
| 2014/0074040 A1 | | 3/2014 | Salto et al. |
| 2014/0114291 A1 | * | 4/2014 | Defossez ........... A61B 17/8872 |
| | | | 604/528 |

FOREIGN PATENT DOCUMENTS

| | | |
|---|---|---|
| EP | 1736191 | 4/2010 |
| JP | 4468664 | 5/2010 |
| KR | 20120136983 | 12/2012 |
| WO | 9632981 | 10/1996 |
| WO | 2013023435 | 2/2013 |

OTHER PUBLICATIONS

Bader et al., The "all-seeing needle": initial results of an optical puncture system confirming access in percutaneous nephrolithotomy, Eur Urol., Jun. 2011; 59(6):1054-9, (epublished Apr. 1, 2011).

Varadarajulu et al., Use of a 19-gauge injection needle as a guide for direct percutaneous endoscopic jejunostomy tube placement, Gastrointest Endosc. Jun. 2003; 57(7):942-5.

Wikipedia Article—Seldinger Technique—Downloaded Mar. 10, 2015, Available online at http://en.wikipedia.org/wiki/Seldinger_technique.

Hee, H.D., Assembly for Biopsy Needle, English Abstract of Korean Patent Publication KR20120136983, Dec. 20, 2012, European Patent Organization, http://www.epo.org/searching/free/espacenet.html.

Botich et al., Safety Stylet for Intravenous Catheter Insertion, English Abstract of European Patent Publication EP0821603, Feb. 4, 1998, European Patent Organization, http://www.epo.org/searching/free/espacenet.html.

Suda et al., Puncturing Needle, English Abstract of Japanese Patent Publication JP4468664, May 26, 2010, European Patent Organization, http://www.epo.org/searching/free/espacenet.html.

Zhang et al., Hardening Injection Needle, English Abstract of Chinese Patent Publication CN201290952, Aug. 19, 2009, European Patent Organization, http://www.epo.org/searching/free/espacenet.html.

Zhang, Y., Secure Vein Puncture Needle, English Abstract of WIPO Patent Publication WO2013023435, Feb. 21, 2013, European Patent Organization, http://www.epo.org/searching/free/espacenet.html.

* cited by examiner

SURGICAL TOOLS AND SYSTEM FOR SAFELY ACCESSING BODY CAVITIES AND METHODS OF USING THE SAME

FIELD OF THE INVENTION

The present invention relates to a surgical system for accessing internal cavities of human or animal for medical treatment and delivering catheter/tube into those cavities. More particularly to surgical needle and sheath systems and device kits for use in minimally invasive surgical procedures and catheter delivery mechanisms, and methods of using the same.

DISCUSSION OF THE BACKGROUND

There are many situations where there is a medical indication to insert a catheter or a tube into a body cavity. For example, with regard to the abdominal cavity, a catheter or tube may be required for various conditions and medical indications, such as peritoneal dialysis, a ventriculo-peritoneal shunt, diagnostic peritoneal lavage, and paracentesis, among other conditions. The insertion of a catheter or tube may also be required in the thoracic cavity for treating various conditions therein, such as pneumothorax, pleural effusion, and hemothorax, among other conditions.

Laparoscopic surgery has replaced open conventional surgery for many invasive procedures because it reduces morbidity, pain, and hemorrhaging due to smaller incisions, and results in shorter hospitalizations. Laparoscopy uses a laparoscope (a thin, lighted tube that includes a camera) put through a small incision in the abdomen created by a needle. The surgeon can view the abdominal organs or female reproductive organs using a camera passed through the tube. Laparoscopy can be used to find cysts, adhesions, fibroids, infection, and other ailments. Tissue samples can also be taken for biopsy through the laparoscope. The laparoscope allows doctors to perform both minor and complex surgeries with a few small cuts in the abdomen. However, conventional laparoscopic techniques pose risks of damaging organs and other tissues within the peritoneal or other cavities, and thus have substantial drawbacks.

The two most common techniques used to gain entry into the peritoneal cavity during laparoscopic general surgery are the blind needle/trocar insertion and open trocar placement under direct visualization. Once entry into the peritoneal cavity has been achieved, gas insufflation is used to establish pneumoperitoneum. The advantages of establishing a pneumoperitoneum include increased distance between the abdominal wall and viscera/vessels and increased resistance of the abdominal wall, allowing the surgeon to establish a surgical cannula (or channel) in the abdominal wall and insert instruments through the cannula without collapsing the abdominal wall on the internal organs and tissues.

Complications associated with operative laparoscopy usually arise from injury to internal structures during abdominal entry. The use of conventional blind needle access can create substantial risks of injury for laparoscopy patients. The drawbacks of establishing pneumoperitoneum also include the risk of bowel or vascular injury and preperitoneal placement of the catheter. The incidence of bowel and vascular injuries is relatively low (about less than 1%). However, a major vascular injury or unrecognized bowel injury carries significant morbidity and mortality rates. Preperitoneal placement of the needle allows for extraperitoneal insufflation of gas which can lead to subcutaneous emphysema and increased distance between the skin and peritoneal cavity making eventual percutaneous placement much more difficult. This may require abandonment of the laparoscopic procedure all together. Gas embolus may occur if a blood vessel is punctured by the needle and the $CO_2$ gas pumped through the needle during insufflation is introduced into the blood vessel. Although rare, a gas embolus is potentially fatal. As a further example, existing techniques for diagnostic peritoneal lavage require a long incision along the linea alba, which results in significant pain and is practically impossible to perform with local anesthesia alone. Improvements in the instruments and techniques used to access the abdominal cavity are needed.

There are also drawbacks to the existing techniques for accessing the thoracic cavity (e.g., to drain fluid in the case of pleural effusion, empyema, hemothorax, etc.). Existing techniques include: 1—blindly accessing the cavity through the thoracic wall with a trocar or cannula, which can result in injury to the tissues within the cavity. Additionally, conventional techniques do not offer minimally invasive systems or methods for quickly accessing body cavities in emergency situations without significant risk of injury. Furthermore, the only acceptable method for evacuating the thorax emergently is by open technique which is associated with significant risks of bleeding, internal organ injury including injury to the lungs, heart, liver, and other organs and tissues. The open surgical techniques are currently used in procedures for accessing the thoracic cavity because all the current minimally invasive techniques require accompanying imaging when used in the thoracic cavity, which is usually not available in emergent situations. Radiographic guided methods may minimize the trauma to the tissue, but such techniques require special expertise, patient transfer to a cath lab or IR suite and necessitate the use of additional costly imaging, which may not be available.

Thus, conventional techniques for accessing and draining fluid from body cavities have high risk of injury due to blind needle insertion and/or require systemic anesthesia. As mentioned above, catheter insertion is currently accomplished by one of two main methods:
1. Open or endoscopic surgical technique, which are associated with can result in unnecessary tissue trauma and pain, an increased time for healing, higher risk of infection and bleeding, and the need for general anesthesia; and
2. Radiographic guided methods that may minimize the trauma to the tissue, but that require special expertise, patient transfer to a cath lab or IR suite, and the use of additional costly imaging, that may not be available.

Therefore, there is a need for new, safer techniques that can be performed more quickly and efficiently at the bedside without the absolute need for systemic anesthesia. It is thus desirable to provide improved catheter/device delivery systems and methods for accessing the peritoneal cavity, the thoracic cavity, and other cavities in the body of humans or animals that reduce the risk of injury. The present invention provides such a catheter/device delivery system and methods of using the same, which include improvements over related conventional technologies and provide desirable results as described below.

SUMMARY OF THE INVENTION

Embodiments of the present invention provide instruments for penetrating a body cavity of a human or animal and positioning instruments therein, and methods of using the same. More particularly, embodiments of the present invention provide needle and cannula systems that are operable to penetrate a body cavity while preventing damage to organs and/or tissues within the cavity, and methods of using or operating the same.

The present invention includes a medical device system and methods of using the instruments thereof for providing minimally invasive procedures that can be efficiently and quickly executed without sacrificing safety. The instruments include a safety needle and a flexible sheath for establishing a small access incision for accessing a targeted body cavity or lumen from the exterior of the body, while reducing injury and morbidity. The surgical instruments of the present invention may further include one or more of the following safety mechanisms: a piercing needle having a sharp outer cannula and an inner blunt, spring-loaded stylet that protrudes and protects internal organs and tissues from puncture or damage, a tension adjustment mechanism for the spring-loaded stylet for adjusting the force required to push stylet into the outer piercing needle, a flexible outer sheath that may be sheathed over the piercing needle during insertion of the needle to gain access to the cavity or lumen, graduations on the flexible outer cannula and other instruments to guide precise placements of various tools, and/or visual and/or auditory indicators to notify the surgeon the needle punctures a body cavity and the stylet extends past the needle point. These safety features lessen the risk of intrathoracic and intra-abdominal injury to organs in procedures where the tool system is used to access the thoracic cavity, abdominal cavity, pelvic cavity, etc.

With regard to the safety needle, the needle structure has a cannula (hollow tube) having a sharp needle edge at its distal end for penetrating superficial tissue and accessing a targeted body cavity or lumen, and a spring-loaded inner stylet having a blunt distal tip. The blunt stylet may sit concentrically and flush within the outer sharp cannula. In the resting state (with no pressure applied to the stylet), the blunt distal end of the stylet may be in an extended position in which the stylet protrudes from the sharp outer cannula such that sharp cutting edge of the sharp outer cannula is not exposed at the end of the needle. The stylet may be pressed into a retracted position within the sharp outer cannula with the application of pressure. The blunt stylet is spring-loaded such that the stylet will return to the extended position, once pressure is no longer applied to the end of the stylet. In use, the needle may be advanced through superficial tissues (e.g., epidermal, adipose, connective tissues, vessel wall, etc.) and the blunt stylet may be pushed into a refracted position in the sharp outer cannula due to the resistance presented by the superficial tissue. Once the outer cannula passes completely through the outer tissue and into the inner lumen or cavity, pressure is relieved on the stylet, allowing it to protrude past the sharp outer cannula to prevent the sharp edge of the cannula from contacting or damaging any tissues within the targeted lumen or cavity. The needle may include one or more indicators (e.g., visual, auditory, etc.) that identify when the pressure on the stylet is released and the stylet extends past the needle point.

The flexible outer cannula may function as a sheath through which the needle may be inserted. The sheath may have a close, flush fit with the needle and may have a slightly shorter length than the cannula of the needle, thereby allowing the sharp needle edge to access the superficial tissue and penetrate the targeted cavity or vessel while the flexible cannula is placed over the needle. The flexible cannula may be made from surgical-grade rubber or other flexible non-reactive, surgical-grade material. In some embodiments, the needle may lock into place within the sheath when the needle is fully advanced into the sheath to prevent slippage of the needle during penetration of the tissues.

In use, the flexible cannula may prevent piercing, lacerating, or other damage that may be caused by using a rigid cannula to establish an access incision into a cavity. The flexible cannula is relatively soft and safe for organs within a cavity, in contrast to rigid and/or sharp metal instruments. The flexible cannula may be graduated with length measurements to indicate to the surgeon the depth to which the cannula and the needle have been advanced into the targeted body cavity. Thus, the graduations may allow the surgeon to determine the depth at which the tip of the cannula penetrates into the body cavity. It would also guide the next steps when using other instruments included in the tools and methods of the invention. In some embodiments, the cannula may be used as a port to introduce a wire through the cannula. The insertion of the wire may be followed by the introduction of a catheter, tube, drain, etc. over the wire and into the access incision. Also, the cannula may be used directly to insufflate or evacuate the cavity into which the cannula has been introduced.

Some embodiments of the invention may also include additional tools having graduations thereon. Such embodiments may include a kit of surgical tools that have coordinated lengths and graduations that allow the surgeon to have precise control over the depth to which the instruments are introduced into a body cavity. The surgeon can thus better avoid causing injuries during the insertion of the tools in the surgical kit. The tools in the surgical kit may include graduated guide wires, dilators, cannulas, and other tools commonly used in an operating room, a cath lab or in an interventional radiology suite.

The novel instruments and methods of the present invention provide a safe and efficient means to establish access to a body cavity without sacrificing safety. The methods are minimally invasive, since they may require only small incisions created by the safety needle, and may require only local anesthesia. Because of the safety profile and the minimally invasive nature of this device, systemic anesthesia may be unnecessary, and the procedures can be performed at the bedside or in an office setting. This efficiency not only cuts down on the time and preparation required to perform the procedures, it also cuts down on the costs associating with the procedures, including costs for facilities, anesthesia, and instruments.

Additionally, because these procedures do not require general anesthesia or an operating room, the surgical instruments of the present invention can be used in broader range of emergency situations and indications that are not currently addressed by available catheter insertion techniques. For example, the surgical tools of the present invention may be used to establish a catheter for a diagnostic peritoneal lavage in unstable patients urgently at the bedside or in the emergency room. Current techniques utilize a larger incision along the linea alba that requires more time, more instruments, and necessitate systemic anesthesia that is impractical at the bedside or in the emergency department. Thus, the safety features of the surgical instruments of the present invention may allow a surgeon or other medical professional to act quickly and safely in an emergency situation to establish a catheter in the abdominal or thoracic cavity for diagnosis and/or drainage (e.g., thoracostomy) or other purposes. Additional features and benefits are discussed below in connection with more specific descriptions of the present invention.

The inventive instruments and methods described herein have the following advantages over conventional instruments and methods:
 a. simplification of catheter delivery into a body cavity,
 b. reduction of the time needed to perform the catheter insertion,
 c. increased safety of the patient, including significant decreases in the tissue trauma associated with conventional methods of catheter delivery,
 d. elimination of the need for general anesthesia, the control of pain through the use of local anesthesia alone, and the minimization of patient discomfort,
 e. optimization of the safety of the delivery of a catheter to the body cavity,
 f. the ability to perform the catheter insertion at a bedside,
 g. elimination of the need for costly imaging equipment and circumvention of the need to coordinate surgical intervention with the busy schedules of the IR suites and/or cath lab, and
 h. reduction in the cost of the insertion procedure in comparison to conventional open or endoscopic surgical techniques, which may also require expensive imaging to guide the procedure.

The inventive instruments and methods described herein may also enhance the utility of catheter placement in certain situations, e.g., it may replace exploratory operation by the use of peritoneal lavage, and increase the utility of peritoneal dialysis as an alternative to hemodialysis, which would enable renal failure patients to be more freedom to travel and keep jobs and curb down the costs associated with hemodialysis.

In one aspect, the present invention relates to a medical device or device kit that includes a cannula assembly having a flexible hollow cannula with a proximal end, a distal end, and an interior diameter; and a needle assembly fitting closely within the hollow cannula and having an outer hollow needle having a proximal end, a sharp distal end, and an exterior diameter that is substantially equal to said interior diameter of the hollow cannula, wherein the outer hollow needle can be snuggly inserted into the cannula, and an inner stylet having a proximal end and a blunt distal end, the inner stylet extending through the outer hollow needle, wherein the needle assembly includes a biasing structure for biasing the stylet to a position where the blunt distal end of the stylet extends beyond the sharp distal end of the outer hollow needle. The instrument kit may further include a guide wire having at least one graduation marking thereon, a dilator having locking tabs, and a cannula having locking notches and graduation markings thereon, wherein the locking notches of the cannula are engageable with the locking tabs of said dilator, allowing the cannula and the dilator to be coupled together and inserted into an incision together.

In a second aspect, the present invention relates to a medical kit for piercing a targeted body cavity without damaging the organs or tissues therein, comprising a safety needle assembly having a sharp outer cannula having an exterior diameter and a distal cutting end, and an inner stylet having a blunt distal end, where the stylet is spring biased to extend from a distal cutting end with sufficient pressure to protrude from the distal cutting end when the distal cutting end penetrates an interior space of the targeted body cavity; a flexible sheath with a proximal end and a distal end and having an interior diameter that is substantially equal to the exterior diameter of the sharp outer cannula of the safety needle, wherein the outer cannula has an inner diameter that is substantially equal to the outer diameter of the outer cannula and fits snuggly into the hollow flexible cannula; and drainage tube assembly that includes a drainage tube and a drainage tube introducer, wherein the drainage tube introducer has a distal head that engages a distal end of the drainage tube and the distal head is configured to dilate an access incision and establish the drainage tube in the cavity of the body cavity. In some implementations, the flexible cannula has a set of graduation markings thereon for determining a depth of the flexible cannula in a body cavity. The drainage tube introducer may include a piercing distal head having an enlarged piercing tip and a wire channel there through, and retention clips that can be detachably engage with the drainage tube. The drainage tube may have a sufficient diameter to both drain viscous fluids from a cavity (e.g., blood, puss, etc.) and allow the distal head of the introducer to be retracted from the targeted cavity through the drainage tube.

In a third aspect, the present invention relates to a method of establishing an access port in a body cavity of an animal or human that includes piercing an outer layer of tissue with a safety needle and flexible sheath assembly to access a targeted cavity, the safety needle and flexible sheath assembly may include a flexible hollow sheath with a proximal end, a distal end, and an interior diameter, and a safety needle fitting closely within the hollow sheath and having an outer hollow needle having a proximal end, a sharp distal end, and an exterior diameter that is substantially equal to the interior diameter of the flexible hollow sheath, wherein the outer hollow needle can be snuggly inserted into the sheath, and an inner stylet having a proximal end and a blunt distal end, the inner stylet extending through the outer hollow needle, where the safety needle includes a biasing structure for biasing the inner stylet to extend the inner stylet from the sharp distal end with sufficient pressure to protrude from the distal cutting end when the sharp distal end penetrates into an interior space of the targeted body cavity, and removing the needle from the flexible hollow sheath once the sheath penetrates the targeted cavity to establish access to the targeted body cavity through the flexible hollow sheath. The method may further include establishing a guide wire in the targeted cavity by threading the guide wire through the flexible sheath, advancing a dilator-cannula assembly into the targeted cavity using the guide wire to guide the insertion of the dilator-cannula assembly, and disengaging the dilator from the cannula and removing the guide wire and dilator to leave the cannula established in the targeted cavity as a surgical access port into the targeted cavity.

In a fourth aspect, the present invention relates to methods of establishing a drainage tube in a cavity of a human or animal for the purpose of draining gas or fluid there from, including piercing an outer layer of tissue with a safety needle and flexible sheath assembly to access a targeted cavity; disengaging the safety needle from the hollow sheath and removing the safety needle therefrom to establish the flexible hollow sheath in the targeted cavity; passing a guide wire through the flexible hollow sheath into the targeted cavity; removing the flexible hollow sheath from the targeted cavity; passing a drainage tube and drainage tube introducer into the targeted cavity using the guide wire as a guide, wherein the drainage tube introducer includes a distal dilating tip that is engaged with a distal end of the drainage tube by one or more retention clips; disengaging the distal head of the introducer from the drainage tube; and drawing the distal end of the introducer out of the targeted cavity through the drainage tube.

It is therefore an object of the present invention to provide surgical tools that can be used to safely access body cavities of humans and animals in a very minimally invasive fashion that prevent or reduce the risk of damaging the internal organs and tissues.

It is an additional object of the present invention to provide surgical tools and methods that reduce the cost and time required for introducing a catheter into a body cavity, without compromising safety.

It is an additional object of the present invention to provide a novel method for accessing the abdominal cavity for a laparoscopic surgery with less risk of damaging internal organs and tissues.

It is an additional object of the present invention to provide surgical tools and methods that allow safe, minimally invasive entry into the abdominal cavity to establish a catheter in the abdomen while using only local anesthesia, without the need for systemic anesthesia.

It is an additional object of the present invention to provide surgical tools and methods that can quickly and safely establish a catheter in the thoracic cavity in emergency situations, e.g., to drain fluids in the event of hemothorax or air in the event of pneumothorax/tension pneumothorax.

It is an additional object of the present invention to provide a novel method for safely accessing the thoracic cavity and establishing a thoracostomy.

It is an additional object of the present invention to provide more efficient tools and methods for accessing body cavities and establishing catheters therein that can be utilized without general anesthesia, allowing the tools and methods to be used without lengthy preparations in urgent and emergency situations.

It is an additional object of the present invention to provide surgical kits that have a precise and integrated unit graduation system to allow a surgeon or other medical professional precisely control the depth to which a surgical instrument is inserted into a body cavity.

It is an additional object of the invention to provide surgical tools and methods that allow a surgeon or other medical professional to access a body cavity that result in less morbidity and reduced recovery time.

It is an additional object of the invention to provide efficient methods that do not require general anesthesia and operating rooms, and that thus cut down on the time and preparation required to perform the procedure and reduce the costs associating with the procedures, including costs for facilities, anesthesia, and instruments.

Additional objects of the invention will be apparent from the detailed descriptions and the claims herein.

DETAILED DESCRIPTION

Figure 1:
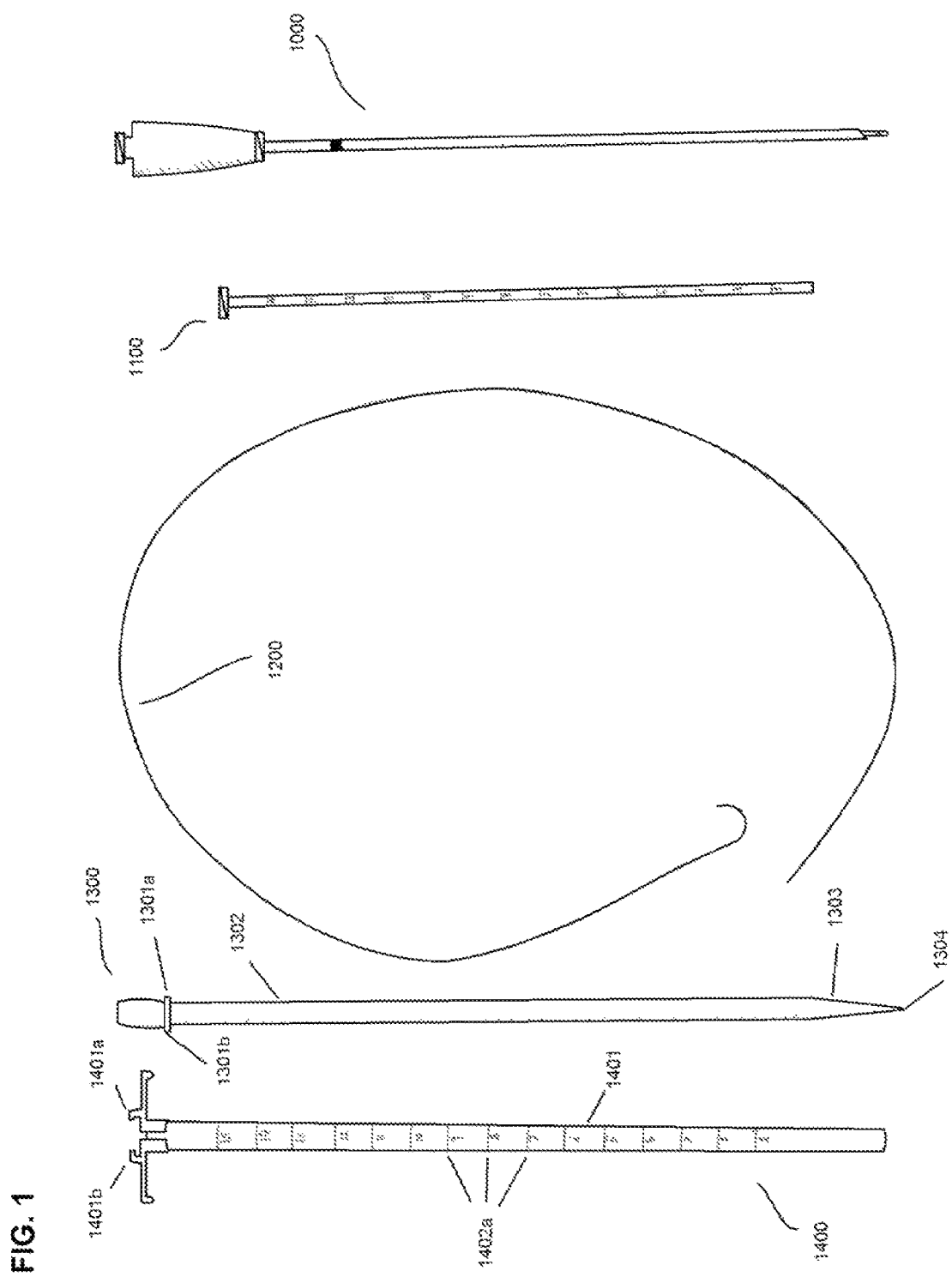
FIG. 1 shows a kit of surgical instruments according to an embodiment of the present invention.

Reference will now be made in detail to certain embodiments of the invention, examples of which are illustrated in the accompanying drawings. While the invention will be described in reference to these embodiments, it will be understood that they are not intended to limit the invention.

To the contrary, the invention is intended to cover alternatives, modifications, and equivalents that are included within the spirit and scope of the invention as defined by the claims. In the following disclosure, specific details are given to provide a thorough understanding of the invention. However, it will be apparent to one skilled in the art that the present invention may be practiced without these specific details.

Referring to the drawings wherein like reference characters designate like or corresponding parts throughout the several views, and referring particularly to FIGS. 1-24, it is seen that the present invention includes various surgical tools for accessing a body cavity and methods of using the surgical tools (see, e.g., FIGS. 1-24). The surgical tools may be included in a kit for particular surgical procedures for safely accessing a body cavity of a human or animal, and the components of the kit may vary to some degree depending on the particular procedure to be performed.

The embodiments of the present invention may include a combination of surgical tools that may be used to access a body cavity in the context of various surgical procedures (e.g., insertion of a peritoneal dialysis catheter, insertion of a ventriculoperitoneal shunt, placing a chest tube in the thoracic cavity, placing a catheter to perform paracentesis, or to perform a diagnostic peritoneal lavage, laparoscopy, etc.). The one or more surgical tools may be included in a kit designed for establishing a catheter in a body cavity (e.g., abdominal, thoracic, etc.). The combination of surgical tools may include a safety needle and a flexible sheath for establishing an access portal into a cavity (e.g., peritoneal cavity, pleural cavity, pericardium, intrathecal etc.) without damaging the tissues therein while allowing the surgeon or other medical profession to completely penetrate the cavity wall and establish a functional access incision. The safety needle may include several safety features, including a sharp outer cannula and an inner spring-loaded blunt tip stylet that protrudes and protects internal organs and tissues from puncture or damage, and a tension adjustment mechanism for the spring-loaded stylet for adjusting the force required to push the stylet into the outer piercing cannula against the tension of the spring, thus allowing different penetrating force for different tissues.

The flexible outer sheath may be sheathed over the safety needle during insertion of the safety needle to gain access to the cavity or lumen. The flexible catheter may be made from a material that is flexible enough (e.g., a surgical grade rubber or other polymeric material) that it can be advanced into the body cavity and contact internal organs and tissues without piercing or lacerating them. Graduation markings may be included on the flexible outer cannula and other instruments for guiding precise placements of various tools within a targeted body cavity. The safety needle may also include visual and/or auditory indicators to notify the surgeon when the outer cannula punctures a body cavity and the stylet extends past the cutting end of the outer cannula. Additional safety features are described herein and are apparent from the following description.

In some embodiments the present invention may include surgical tools that may be used in conjunction with the safety needle and flexible sheath, including dilators and rigid cannulas for establishing an access port to the targeted cavity. The present invention may also include additional tools for establishing a drainage tube for draining fluid and relieving pressure from a cavity (e.g., for emergency situations, such as diagnostic peritoneal lavage, pleural effusion, or hemothorax, etc.). The one or more surgical tools may be included in a kit for use in various procedures (e.g., insertion of a peritoneal dialysis catheter, insertion of a ventriculoperitoneal shunt, insertion of a diagnostic peritoneal lavage catheter, thoracostomy procedures, etc.). The surgical tools of the present invention are minimally invasive, creating small incisions, and can be used in various procedures with local anesthetics, without the need for general anesthesia. Because general anesthesia may not be required, the surgical tools of the present invention may be used quickly and safely at the bed side in a medical office, a regular hospital bed, or an examination room without the need to utilize a cath lab, prepare an operating room or interventional radiology suite for the procedure. Additional features and benefits of the present invention are described herein and are apparent from the following description.

Instrument and Kit Embodiments

Some embodiments of the present invention include surgical tools and surgical tool kits that include a safety needle and flexible sheath for accessing a body cavity without damaging the organs and tissues therein, and methods of using such surgical tools and kits. The safety needle and flexible sheath may be used to safely establish an access portal into a body cavity (e.g., the abdominal cavity, the pelvic cavity, etc.), and additional tools may be used to establish a trocar or other port through which instruments or catheters may be passed. In some embodiments, a drainage tube may be established in the access portal established by the safety needle and flexible sheath in order to drain fluids or gases from the body cavity (e.g., in the case of pleural effusion, hemothorax, ascites, etc.). The flexible sheath and additional other tools may have graduation markings thereon (e.g., length unit markers, indicating length in one or more units, such as centimeters, millimeters, inches, etc.) to allow the surgeon or other medical professional to precisely control the depth to which the surgical tools are advanced into the cavity and to determine the length to which the other parts of the kit should reach in order to be in the cavity without causing any organ injury.

The safety needle and the flexible sheath may be designed to be coupled together for the purpose of piercing the body wall and establishing the flexible sheath in the body wall and within the targeted cavity, where the flexible sheath may fit snugly over the safety needle and be secured to the safety needle during the step of piercing the body wall. In the process of establishing the access portal into the targeted cavity (e.g., the peritoneal cavity), the piercing needle may be advanced to a depth that is sufficient to pierce the body wall and, optionally, membranes lining the targeted cavity (e.g., in the case of the abdominal cavity, the safety needle may be advance to the point that it pierces the peritoneum), but shallow enough to avoid damaging the organs (e.g., the aorta and the major vessels in the retroperitoneum). The surgeon or other medical professional using the piercing needle/flexible sheath combination may be notified of the depth and position of the piercing needle by observing (1) graduation markers on the exterior surface of the flexible sheath, and/or (2) one or more safety indicators built into the safety needle that indicate when the blunt stylet extends past the cutting end of the sharp outer cannula of the safety needle (e.g., a visual indicator, an audible indicator, and/or other additional indicators). The flexible sheath may have a length that is nearly the same length as the sharp outer cannula of the safety needle, such that only a small portion of the end of the sharp outer cannula protrudes beyond the end of the flexible sheath when the flexible sheath is positioned over the needle. Consequently, the flexible sheath may be established within the targeted cavity when the safety needle penetrates the cavity. For example, and without limitation, only small portion of the sharp outer cannula (e.g., the sharpened end thereof) and the blunt end of the blunt stylet (which protrudes from the sharp outer cannula) may protrude beyond the flexible sheath, once the safety needle and the flexible sheath enter the targeted cavity.

Figure 12:
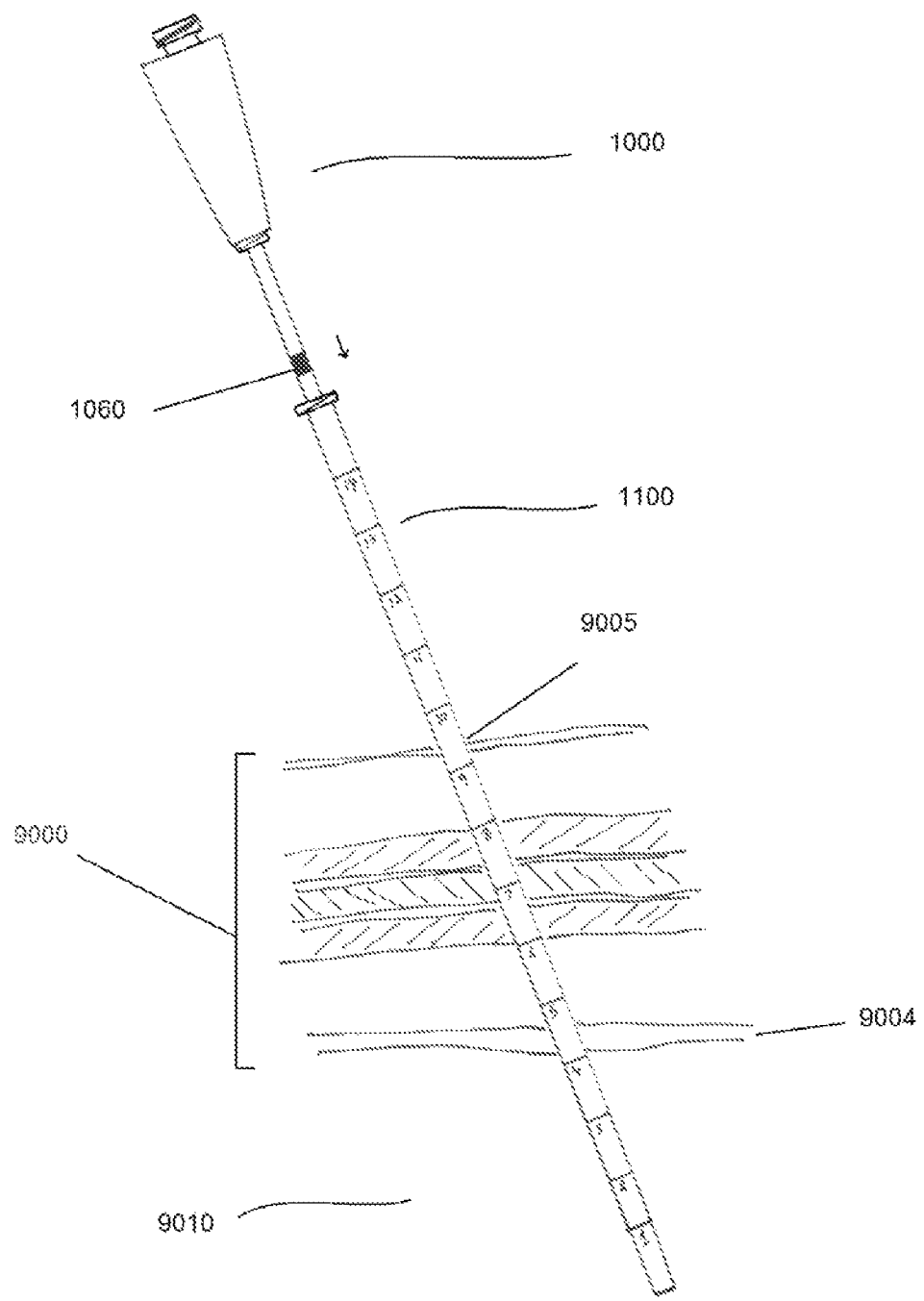
FIG. 12 shows a step of disengaging a flexible sheath from a safety needle and advancing the flexible sheath into a targeted cavity according to an embodiment of the present invention.

Once the safety needle and sheath are established within the targeted cavity, the sheath may be advanced over the sharp outer cannula and further into the cavity until a depth marker on the sharp outer cannula can be observed (see, e.g., position/depth marker 1060 in FIG. 12). At that point, the portion of the sharp outer cannula that is within the cavity may be completely covered by the flexible sheath. The safety needle can then be withdrawn from the sheath and the cavity without advancing the sheath further into the cavity, to thereby establish the sheath as a safe access port to the cavity. A wire may then be passed through the sheet and into the cavity. Once the wire is in, sequential steps will enable the surgeon or other medical professional to insert a wide range of catheters, instruments, ports, etc.

Without limiting the invention, FIG. 1 illustrates an exemplary surgical kit that includes instruments that may be used for minimally invasive procedures in which a small access incision may be established for accessing a targeted cavity. The surgical kit may include a safety needle 1000, a flexible outer sheath 1100, a guide wire 1200, a dilator 1300, and a cannula 1400. The kit may include further instruments, as discussed herein. Detailed discussions of the individual instruments in the kit are provided below.

Figure 2:
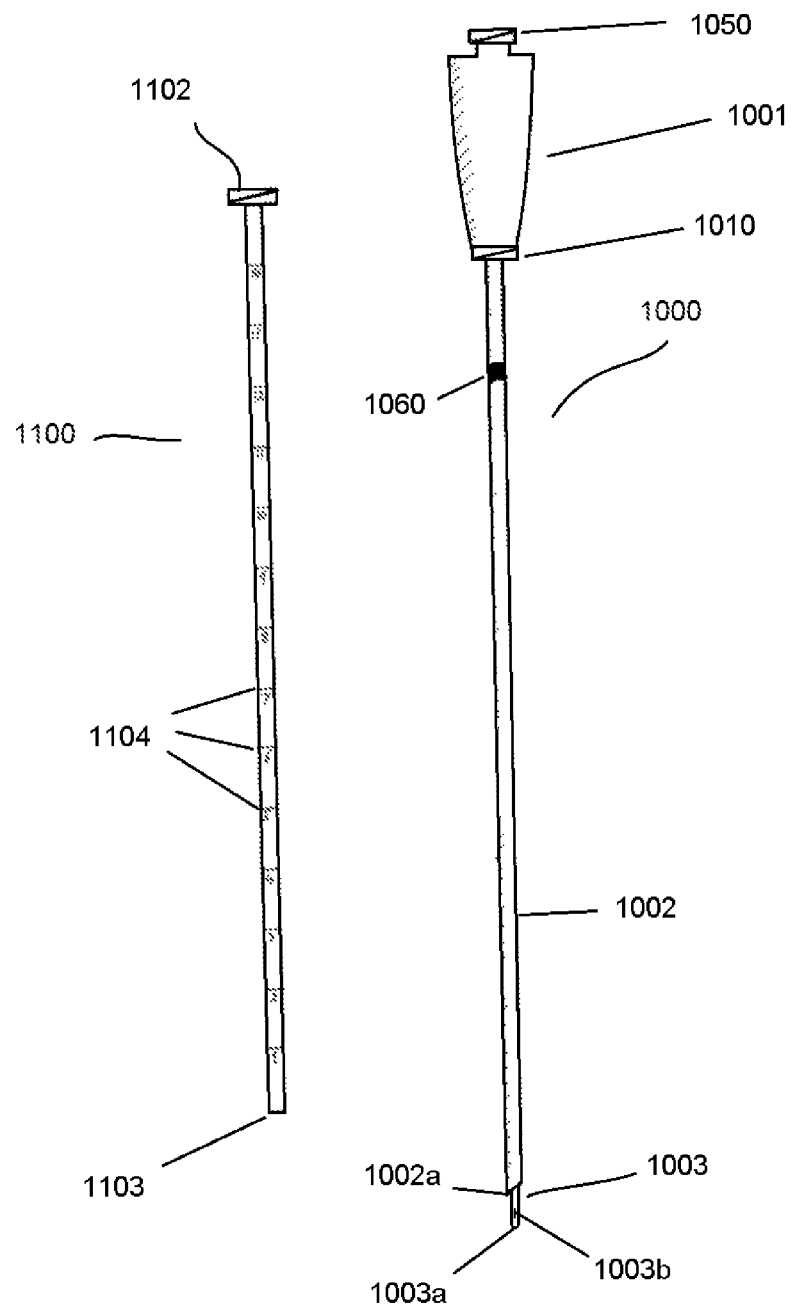
FIG. 2 shows a safety needle and flexible sheath according to an embodiment of the present invention.

Without limiting the invention, FIG. 2 shows an example of a paired safety needle 1000 and a flexible outer sheath 1100, which may be used in conjunction to safely penetrate a body cavity during a surgical procedure. The safety needle 1000 may include a handle 1001, a sharp outer cannula 1002 that includes an oblique sharpened cutting edge 1002a for piercing a cavity wall, and a blunt inner stylet 1003 that includes a blunt safety end 1003a and a distal insufflation hole 1003b. In some embodiments, and without limiting the invention, the needle and blunt stylet may be produced from stainless steel via various processes (e.g., high temperature extrusion, a drawn wire process, etc.).

Figure 3:
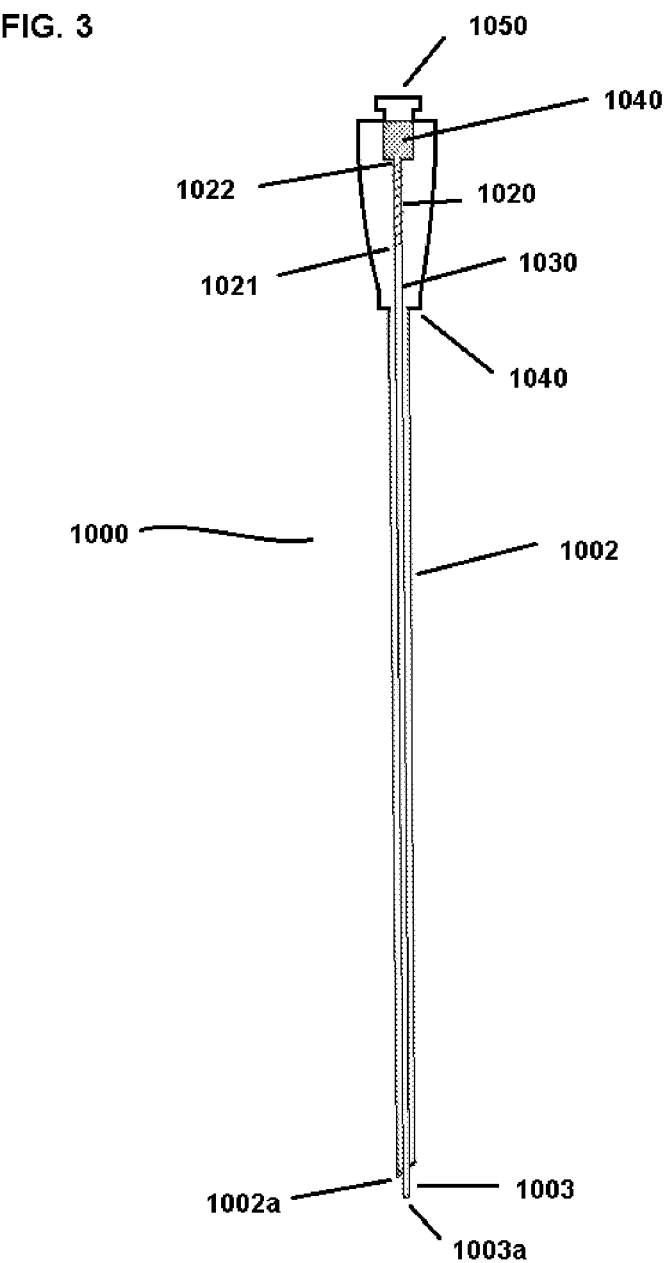
FIG. 3 shows a cross-sectional view of a safety needle according to an embodiment of the present invention.

Without limiting the invention, FIG. 3 shows a cross-sectional view of an exemplary safety needle 1000, providing views of internal structures within the safety needle 1000. The spring 1020 is present in a central channel 1030 within the handle 1001 of the safety needle 1000. The blunt stylet 1003 is nested within both the central channel 1030 and the spring 1020. The blunt stylet may have a one or more catches, lips, or other protrusions at resistance point 1021 along the blunt stylet, against which the spring may apply force pushing the blunt stylet distally toward the end of the safety needle 1000. The opposite end of the spring 1020 may abut a lip, rim, or slot at resistance point 1022. This arrangement of the spring 1020 allows it to exert increased force to push the blunt stylet 1003 distally at resistance point 1021 when the spring 1020 is compressed. In other implementations, the spring may be anchored to the central canal 1030 at an anchoring point 1021, which may be a slot into which the end of the spring 1020 is inserted and wound, and the blunt probe 1003 may include one or more ridges, lips, or other protrusions at resistance point 1022 at distal end of the blunt stylet, such that the spring is stretched rather than compressed when the blunt stylet 1003 is pressed into the outer cannula 1002 and the spring 1020 pulls the blunt stylet distally at resistance point 1022. Still other implementations and tension mechanisms are within the scope of the present invention.

The safety needle 1000 also includes a cavity 1040 into which the proximal end of the blunt stylet 1003 may be pushed when pressure is applied to the distal blunt tip 1003a of the blunt stylet 1003 (e.g., when the safety needle 1000 is being used to puncture the wall of a cavity). The blunt stylet may have collar or enlarged end at the proximal end thereof for catching on the proximal end of the central channel 1030, so as to prevent the blunt stylet from being ejected from the distal end of the safety needle 1000. Alternatively, reference 1040 may be an enlarged distal portion of the blunt stylet 1003 or a separate structure to which the blunt stylet 1003 is connected having a greater diameter than the portion of the blunt stylet nested within the central channel 1030. In such embodiments, and without limitation, the enlarged proximal end 1040 of the blunt stylet 1003 moves outward from the handle 1001 when the blunt tip 1003a is pressed into the outer cannula 1002, and provides a visual indicator as to when the blunt stylet is retracted and extended.

The flexible sheath 1100 includes a long flexible shaft 1101, which may include graduation markings 1104 on its exterior that may be in one or more units of length (e.g., one or more scales of mm, cm, inches, etc.). The graduation markings may be mold-formed or added by embossing, printing, or other methods. The flexible sheath may be a molded piece made from a flexible material, such as a surgical grade rubber or other polymeric material (e.g., medical grade silicone, nitinol, polyurethane, polyethylene terephthalate (PETE) latex, nylon, or thermoplastic elastomers, etc.).

The safety needle 1000 and the flexible outer sheath 1100 may also include connectors for coupling the flexible outer sheath with the safety needle 1000 to form a single structure that can be passed through the cavity wall and into the targeted cavity. The connectors may have various means of securement (e.g., threading, snap-fitting, pressure-fitting, etc.). Without limiting the invention, the example shown in FIG. 2, the safety needle 1000 may include a threaded connector 1010, which may be coupled with the threaded connector 1102 of the flexible sheath 1100 (e.g., connector 1010 is male threaded connector and connector 1102 is a female threaded connector). When the flexible sheath 1100 and the safety needle 1000 are secured together, the flexible sheath 1100 may fit snugly over the sharp outer cannula 1002, such that the coupled safety needle 1000 and flexible sheath 1100 can penetrate the cavity wall without the flexible sheath catching on any tissues, peeling away from the safety needle, or allowing any tissues to lodge between the sharp outer cannula 1000 and the flexible sheath 1100. For example, the difference between the outer diameter of the sharp outer cannula and the inner diameter of the flexible sheath may be less than about 500 µm (e.g., in a range of about 25 µm to about 400 µm, in a range of about 50 µm to about 300 µm, or any value or range of values therein).

The spring-loaded blunt stylet provides a safety mechanism to the safety needle by protruding from sharp outer cannula whenever the force applied to the blunt end of the stylet is less than the force exerted by the spring tension pushing the blunt stylet outward. To illustrate, when the safety needle is pressed against the outer wall of a body cavity (e.g., the patients skin), and the physician applies sufficient force to pierce the body wall, the force applied by the skin to the end of the blunt stylet may be sufficient to push the stylet into the sharp outer cannula. When the needle passes through the body wall (and optionally, the membranes therein, such as the peritoneum), the safety needle enters the intraperitoneal space, at which point the end of the needle enters a the potential space therein, the force applied to the blunt probe is removed, and the tension in the spring forces the blunt probe to protrude from the end of the sharp outer cannula.

Figure 4:
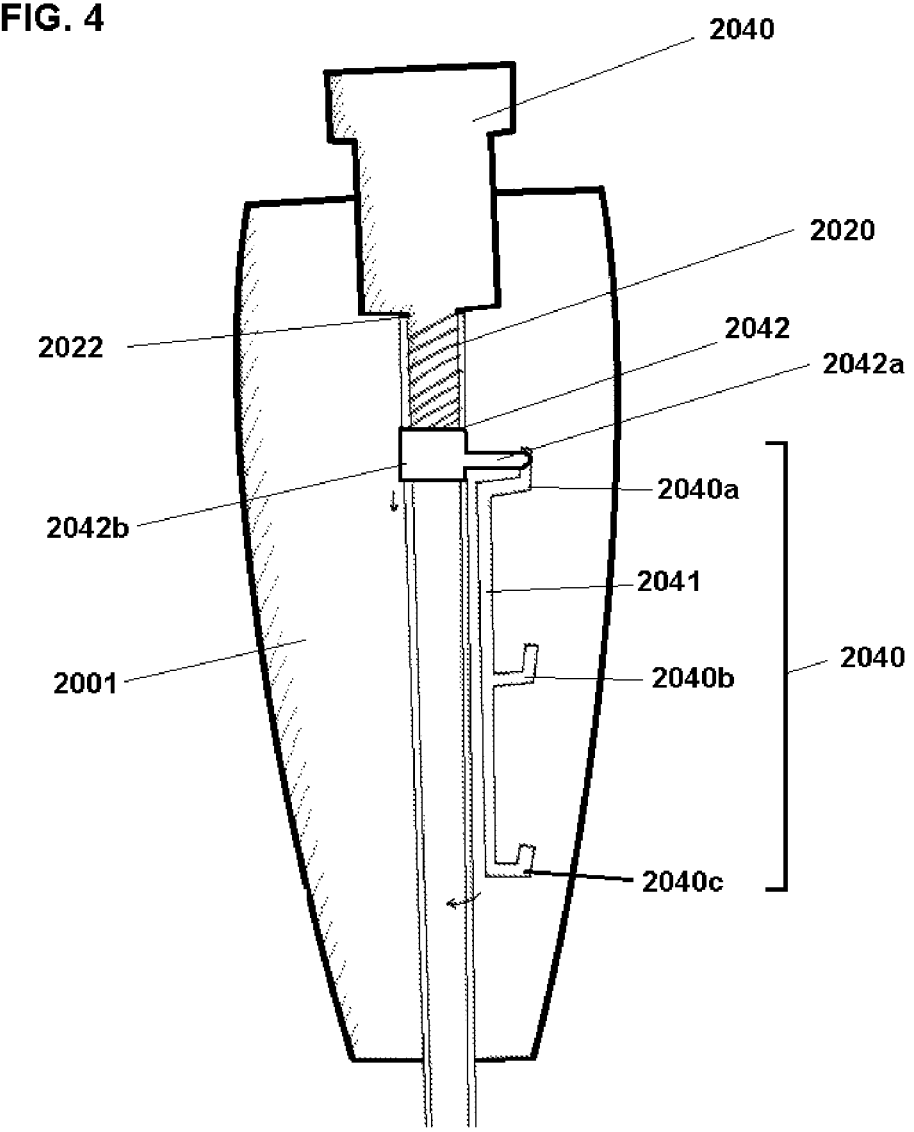
FIG. 4 shows a cross-sectional close up view of a handle and tension adjustment system of a safety needle according to an embodiment of the present invention.

Without limiting the invention, FIG. 4 shows an alternative implementation of a safety needle 2000, in which the tension on the spring 2020 may be adjusted in order to accommodate patients having cavity walls of different thicknesses, patients having different muscle tones, or different body cavities. The adjustment in the tension of the spring results in more or less force required to maintain the blunt stylet within the outer cannula. More force may be required for thicker cavity walls that will result in more tissue being compacted into the sharp outer stylet. The added force allows the blunt style to eject such tissue from the sharp outer cannula once the needle penetrates the cavity. The added force may be important in that it allows the blunt stylet to protrude distally from the outer cannula and prevent the sharp distal cutting edge of the outer cannula from piercing organs and tissues within the targeted cavity.

FIG. 4 shows a close-up, cross-sectional view of the proximal section of an exemplary safety needle 2000, including the handle 2001, and tension adjustment system 2040 that allows the user of the safety needle 2000 to adjust the tension in the spring 2020. The tension adjustment system 2040 may include a slot system 2041 having multiple stopping points (2041a, 2041b, and 2041c), a moveable tension adjustment lever 2042 that can be engaged with the stopping points. The tension control lever may be accessible by the user on the outside surface of the handle 2001 (e.g., the end of the lever may protrude from the handle). The user may disengage the tension adjustment lever 2042a and move it from setting to setting.

Without limiting the invention, the example shown in FIG. 4 shows the tension adjustment lever 2042 having a lever 2042a for engaging with the stopping points 2041a, 2041b, and 2041c, and a spring coupler 2042b. The distal end of the spring 2020 may be nested within and attached to the spring coupler 2042b (e.g., the spring coupler may have an annular slot therein for receiving the distal end of the spring 2020). The proximal end of spring 2020 may be attached to the blunt stylet at attachment point 2022 In this example, the lowest tension setting is at stopping point 2040a (the spring is stretched the least), the highest tension setting is at stopping point 2040c (the spring 2020 is stretched the most), and stopping point 2040b is an intermediate setting. It is to be understood that FIG. 4 provides an example of a tension adjustment system, and that other implementations of a tension adjustment system are within the scope of the present invention. For example, in other implementations, the tension adjustment system may be configured such that the spring pushes blunt stylet distally, rather than pulling it out (as in the example of FIG. 3). In such implementations, the spring may be compressed between a lip or rim on the blunt stylet at or near the end of the central channel of the safety needle (e.g., like safety channel 1030) and the spring coupler (e.g., like spring coupler 2042b), such that the spring pushes the blunt stylet outward. It is to be understood that the resting length of the spring in such an example may be longer than the resting length of the spring in the example of FIG. 4, and that the resting length of the spring may be varied depending on the whether the spring is used to push or pull the blunt stylet in a particular implementation.

Figure 5:
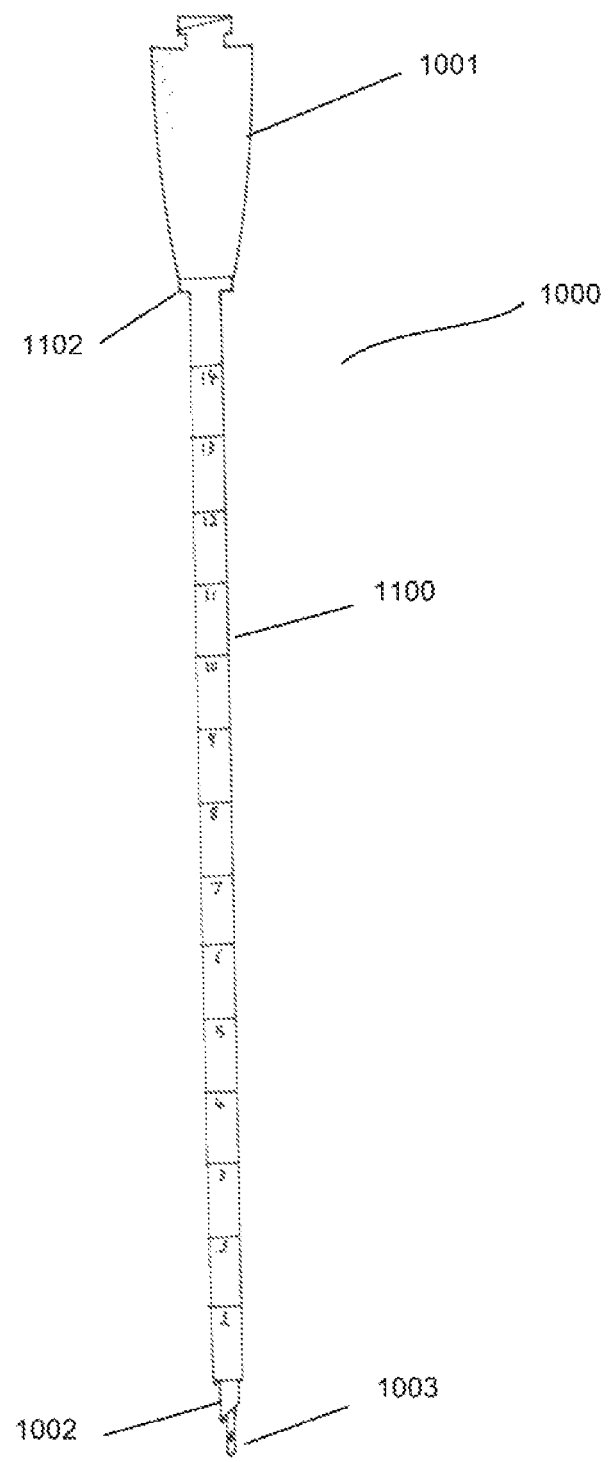
FIG. 5 shows a safety needle and a flexible sheath according to an embodiment of the present invention, with the safety needle and flexible sheath coupled together.
Figure 6:
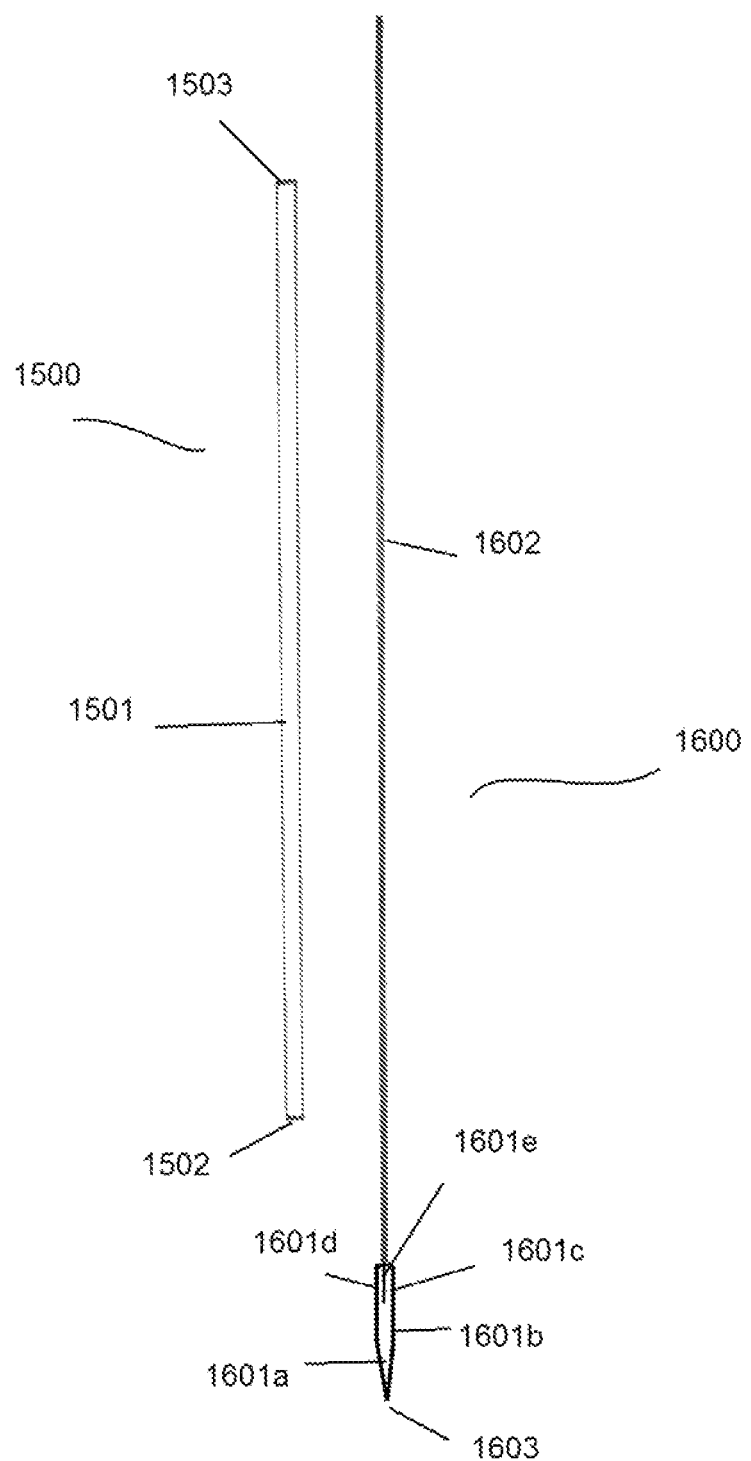
FIG. 6 shows a drainage tube and drainage tube introducer according to an embodiment of the present invention.

Without limiting the invention, FIG. 5 shows a safety needle 1000 coupled with a flexible sheath 1100, with connector 1102 of the flexible sheath 1100 connected to connector 1010 (obscured by connector 1102) of safety needle 1000. It can be seen in FIG. 5 that the length of the flexible sheath 1100 is nearly as long as the portion of the outer cannula 1002 of the safety needle 1000. Only the sharp cutting edge 1002a and a small section of the distal end of the outer cannula extend from the flexible sheath 1100. The lengths of the outer cannula 1002 and the flexible sheath 1100 nearly matched so that the flexible sheath 1100 is introduced into a target cavity to essentially the same depth as the outer cannula 1002 when the coupled safety needle 1000 and flexible sheath 1100 are inserted into a body cavity, which may avoid a shallow placement of the flexible sheath 1100 (e.g., outside the peritoneum). In the example shown in FIG. 5, and without limitation, the exterior of the flexible sheath includes a ruler (e.g., in cm units) thereon to indicate the depth of the flexible sheath 1100. The distal end of the safety needle, including the distal end of the sharp outer cannula 1002 and the cutting edge 1002a, and the distal end of the blunt stylet 1003a may protrude from the end of the flexible sheath 1100 when the safety needle 1000 and the flexible sheath 1100 are coupled together. In the example of FIG. 5, the distal end of the outer cannula 1002 extends about one half centimeter beyond the distal end of the flexible sheath 1100, and the distal end of the blunt stylet 1003 may extend about one half centimeter beyond the distal end of the sharp outer cannula 1002. In the example of FIG. 5, the total length of the portion of the safety needle that extends from the handle 1001 may be about 16 cm, and the length of the portion of the flexible sheath 1100 that is tightly sheathed over the sharp outer cannula 1002 may be 15 centimeters. It is to be understood that the length of the sharp outer cannula, the blunt stylet, and the flexible sheath may be varied in other implementations of the invention, including their relative lengths. It should also be understood that the sharp outer cannula may be slightly longer than the flexible sheath (e.g., enough such that the sharpened cutting edge extends completely beyond the distal end of the flexible sheath).

Once the coupled safety needle and sheath are established in the targeted cavity, the safety needle can be removed from the flexible sheath and additional instrumentation may be used to establish a port to the cavity through which instruments may be passed. The one or more instruments in the cavity accession kit may include additional instruments that are used to establish the instrument port for passing instruments into the targeted cavity for various procedures (e.g., placing a dialysis catheter, placing a ventriculoperitoneal shunt, placing a catheter for paracentesis, etc.), including a guide wire, a dilator, and a cannula. The guide wire 1200 may be passed through the flexible sheath, once the safety needle has been removed therefrom, and into the targeted cavity. The guide wire may include graduation markings thereon (e.g., a scale having one or more units of length, such as cm, mm, inches, etc.) for marking the depth to which the guide wire has been advanced through the flexible sheath. The graduation markings may match the units present on the flexible sheath. The guide wire may have multiple graduation markings or a single mark (e.g., at 20 cm from the distal of the guide wire) to indicate to the user that the guide wire has been advanced a sufficient distance into the targeted cavity. The guide wire may have a flexible and resilient construction, which prevents damage to organs and/or tissues that it contacts when it is advanced into the targeted cavity. It may also include a flexible hook at its end to prevent it from being inadvertently removed from the cavity (e.g., it will catch on the access incision if it is inadvertently pulled toward the exterior of the targeted cavity).

The one or more instruments in the cavity accession kit may also include a dilator and cannula that may be inserted into the targeted cavity over the guide wire. In some embodiments, and without limitation, the dilator and the cannula may be configured to be coupled together and inserted into the access incision as a single unit. The dilator may have a long cylindrical body, a proximal section that may connect to the cannula, and a distal tapered end for dilating the access incision. The dilator may also include a central canal through which the guide wire may be threaded, allowing the guide wire to be used to guide the dilator through the access incision and into the targeted cavity. The dilator may be made from a metal (e.g., but not limited to, stainless steel or aluminum), a composite material (e.g., but not limited to, carbon fiber composite), polymer materials (e.g., but not limited to, medical grade polypropylene, medical grade polycarbonate, etc.).

The cannula may include a hollow cylindrical body that fits snuggly over the cylindrical body of the dilator, and which have a length that equal to or slightly shorter than the length of the cylindrical body of the dilator. The cannula may have a rigid construction and thin walls (e.g., having a thickness in a range of about 0.1 mm to about 1, about 0.3 mm to about 0.7 mm, or any value or range of values therein). The thin walls of the cannula may result in a low profile when the cannula is coupled with and positioned over the dilator, thereby preventing or reducing damage to the tissues surrounding the access incision when the coupled dilator and cannula are inserted through the access incision. The distal end of the cannula may also be tapered in order to further reduce any potential damage to the tissue. The cannula may be made from a metal (e.g., without limitation, stainless steel or aluminum), a composite material (e.g., without limitation, carbon fiber composite), polymer materials (e.g., without limitation, polyether ketone (PEEK), ultra high molecular weight polyethylene (UHMWPE)). It may be desirable to make the cannula from a radiolucent material such as polyether ether ketone (PEEK).

The cannula may also have connector at the proximal end of the cylindrical body for coupling the cannula to the dilator, and one or more handles or grips to allow the surgeon to grasp and manipulate the position of the cannula. Various mechanisms for coupling the dilator and cannula may be utilized, such as threaded connectors, a twist locks with locking tabs, a Storz-style lock mechanisms, etc.

In other embodiments, the dilator may be passed over the guide wire and into the access incision before the cannula is passed over the dilator. In still further embodiments, the cavity accession kit may include multiple dilators that are successively passed over the guide wire before the cannula is passed over the dilators through the access incision.

Without limiting the invention, FIG. 1 shows an example dilator 1300 and example cannula 1400 that are configured to be coupled together prior to insertion into an access incision to a targeted cavity. The dilator 1300 is to be inserted into the cannula 1400 and secured therein prior to insertion over the guide wire. The tapered distal end of the dilator may be inserted into the proximal end 1401 of the cannula 1400 and advanced until it protrudes from the distal end of the cannula. The dilator may include proximal locking tabs 1301a and 1301b that are configured to interlock with notches 1401a and 1401b at the proximal end 1401 of the cannula 1400. The dilator 1300 can be inserted through the cannula 1400 until the tabs 1301a and 1301b are flush with the proximal end 1401 of the cannula 1400 and the dilator can then be rotated until the tabs 1301a and 1301b engage with the notches 1401a and 1401b, thereby locking the dilator 1300 into position within the cannula 1400 prior to insertion into an access incision. The cylindrical shaft 1402 of the cannula 1400 may have a length that is equal to or slightly shorter than the cylindrical body 1302 of the dilator (e.g., without limitation, less than about a 0.1 cm to about 0.5 cm shorter). The cannula 1400 may include graduation markings on its exterior, which may be in various units (e.g., without limitation, a scale of 15 cm on the exterior surface of the cylindrical shaft 1402), allowing the user to monitor the depth to which the cannula and the dilator 1300 have inserted into the access incision.

The tapered end of the dilator 1303 may protrude from the distal end of the cannula 1400, allowing the tapered end 1303 to dilate the access incision as the surgeon or other medical personnel passes the coupled dilator 1300 and 1400 through the access incision. The dilator 1300 includes a central canal 1304 that runs from the proximal end to the distal end of the dilator, allowing the guide wire 1200 to be threaded through the dilator 1300 prior to the insertion of the coupled dilator 1300/cannula 1400 combination into an access incision. The guide wire 1200, once established in the access incision, may be used to guide the dilator 1300 through the access incision and into the targeted cavity.

The one or more surgical instruments of the present invention may include additional instruments that may be used to establish a tube in the targeted cavity that may be used to drain fluids (e.g., without limitation, viscous fluids, such as blood and/or puss, or air, bile, ascitic fluid, etc.). Such additional instruments may be particularly useful in emergency situations when the presence of fluids in a body cavity present an immediate danger to a patient (e.g., without limitation, the establishment of a thoracostomy to drain fluid from the pleural cavity, or a peritoneal catheter for a diagnostic peritoneal lavage). In such situations immediate access to the affected cavity is ideal, and delays that may result from the administration of general anesthesia and/or the preparation of an operating room, cath lab, radiology suite, etc. my cause further risk of injury to the patient. The additional instruments may include a drainage tube and a drainage tube introducer that both dilate an initial access incision established by the safety needle and may also attach to the drainage tube and introduce it into the targeted cavity. The drainage tube and introducer combination can be quickly and safely inserted through the cavity wall to establish the drainage tube in the cavity, allowing the drainage tube to drain the fluid within the cavity.

The drainage tube may be made from a medical grade material, such as a polymer material. For example, and without limitation, the drainage tube may be made from medical grade silicone, polyether ether ketone (PEEK), ultra high molecular weight polyethylene (UHMWPE). In some implementations, and without limitation, the material of the drainage tube may be radio translucent, but may also include one or more radio-opaque markers thereon, so that the tube can be identified on an X-ray image or other diagnostic image. In other implementations, the material of the drainage tube may be made solely from a radiolucent material such as PEEK. In some implementations, and without limitation, the drainage tube may be flexible and soft, and may be used for draining low viscosity fluids from a cavity (e.g., draining ascitic fluid, draining pleural effusion, etc.). In some implementations, and without limitation, the material of the drainage tube may be rigid or semi-rigid to prevent kinks or deformations during the insertion of the drainage tube into the targeted cavity and to hold its shape at larger diameters, which may be utilized for draining more viscous fluids from a cavity (e.g., draining blood in the case of hemothorax, draining puss in the case of empyema, etc.). Without limiting the invention, the drainage tube may have a diameter in a range of about 9 French to about 38 French (e.g., about 28 French to about 38 French, about 12 French to about 28 French, or any value or range of values therein). The drainage tube may have graduation markings on the exterior thereof (e.g., length unit markers, indicating length in one or more units, such as centimeters, millimeters, inches, etc.) to allow the user to monitor the depth to which the drainage tube is advanced into the targeted cavity. The drainage tube may also include a hub at a proximal end thereof that adapts to suction drainage systems and/or other instruments.

The drainage tube introducer may be adapted to be engaged to the distal end of the drainage tube and may function both to dilate an established access incision and to lead the drainage tube into the targeted cavity. In some implementations, and without limitation, the drainage tube introducer may also be configured to be disengaged from the drainage tube and pulled out of the targeted cavity through the drainage tube after the drainage tube is established within the targeted cavity. In such implementations, the diameter of the drainage tube introducer when collapsed must be less than the diameter of the drainage tube.

The drainage tube introducer may include a distal head having a tapered dilator and an expandable retention clip for engaging the distal end of the drainage tube and holding it in connection with the introducer as the introducer is passed through the access incision. In some implementations, and without limitation, the distal end of the drainage tube introducer may have a maximum diameter that is less than the interior or smallest diameter of the drainage tube. The retention clip may be at the proximal end of the distal head and may be expandable such that it can clip to the outer diameter of the drainage tube and shield the drainage tube during insertion into the targeted cavity. The distal head of the introducer may have a conical shape or a distal tip with conical shape, such that when the distal head is expanded it has a cone- or wedge-like shape that prevents tissue and fluid from interceding between the distal head of the introducer and the drainage tube as the distal head is advanced through the access incision.

The retention clip may be an integrally molded piece formed with the tapered dilator, which may or may not be combined with additional structures (e.g., springs, etc.). The retention clip may include two or more radially flexible sections that allow the clip to expand to encompass drainage tubes of various diameters (e.g., without limitation, up to 38 French). In some implementations, the dilator and retention clip portions may be made from a highly resilient material (e.g., a resilient polymer material) that allows the clip to resile (collapse) after it is disengaged from the end of the drainage tube to its original shape. In other implementations, the two or more flexible sections may be connected by springs to each other, to a central wire channel running through the distal head, and/or other structures in the introducer. In various implementations, additional materials may be present between the two or more flexible sections, such as thin polymer layers that are stretchable or collapsible and/or that can expand as the two or more radially flexible sections are moved outward to engage the diameter of the drainage tube, thereby preventing the formation of gaps between the radially flexible sections. In various implementations, the resumption of the original shape may be necessary to allow the distal head to be drawn back through the drainage tube, once the drainage tube is established in the targeted cavity.

The drainage tube introducer may also include a central guide wire channel that connects with the distal head of the introducer between the two or more radially flexible sections and runs through the distal head to the end of the distal end of the introducer. The central wire channel may run from the distal end of the head to the proximal end of the central guide wire channel, and may allow the guide wire to be threaded through the drainage tube introducer so that it can be used to guide the insertion of the introducer and the drainage tube into the targeted cavity to a controlled depth to avoid contact or damage to the internal organs and tissues. The guide wire may have one or more length or graduation markers thereon for determining the depth to which the drainage tube introducer has been advanced into the targeted cavity and allowing the surgeon to control the depth to which the introducer is inserted. Also, the wire channel may be longer than the drainage tube, allowing the user to pull the introducer through the drainage tube after the introducer and drainage tube have been established in the targeted cavity, and the distal head of the introducer has been disengaged from the distal end of the drainage tube.

Without limiting the invention, FIGS. 6-9 show examples of the drainage tube and drainage tube introducer: drainage tube 1500 and introducer 1600. The drainage tube 1500 may have a uniform diameter throughout its length with a distal end 1502 for engaging with the introducer 1600 and a proximal end through which fluid may be drained from a targeted cavity. In some implementations, the proximal end 1503 of the drainage tube may be connected to a hub adapted for connecting to suction drainage systems and/or other instruments (not shown).

The introducer 1600 may include a distal head 1601 and a central guide wire tube 1602. The distal head 1601 may itself include a dilating tip 1601a, a body 1601b, and retention clips 1601c and 1601d. A guide wire canal 1603 may run the entire length of the introducer 1600, from the proximal end of the central guide wire tube 1602 to the tapered distal end of the dilating tip 1601a. The distal head 1601 of the introducer 1600 may be an integrally molded structure made from a resilient material (e.g., a resilient polymer material). The retention clips 1601c and 1601d may be separated from each other along slit 1601e. There may be an additional slit (obscured) on the opposite side of the distal head 1601 from the slit 1601e, separating the two retention clips 1601c and 1601d such that they can be stretched radially outward and receive the distal end 1502 of the drainage tube 1500.

Figure 7:
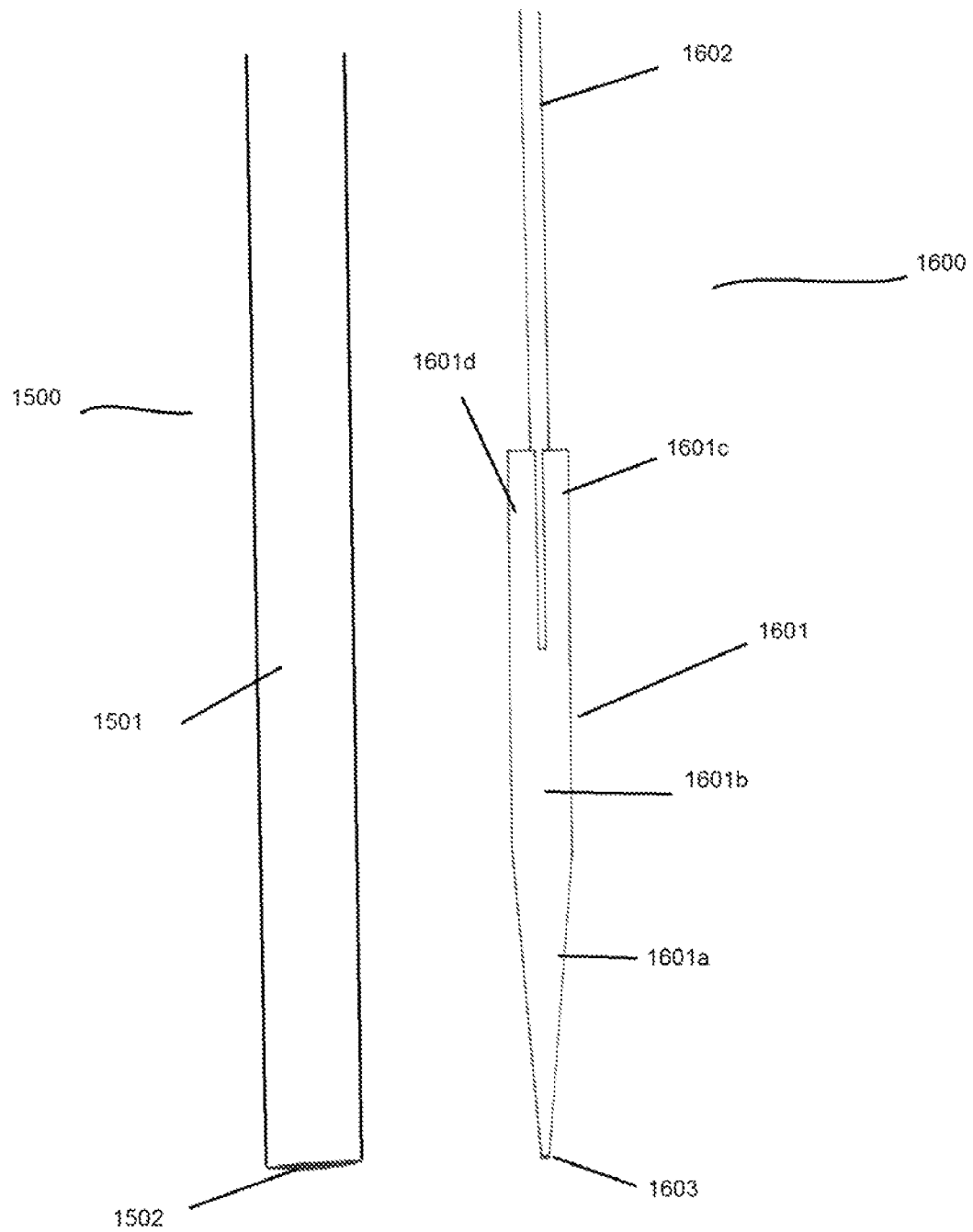
FIG. 7 shows a close-up view of the distal end of a drainage tube and a distal end of a drainage tube introducer according to an embodiment of the present invention.
Figure 8:
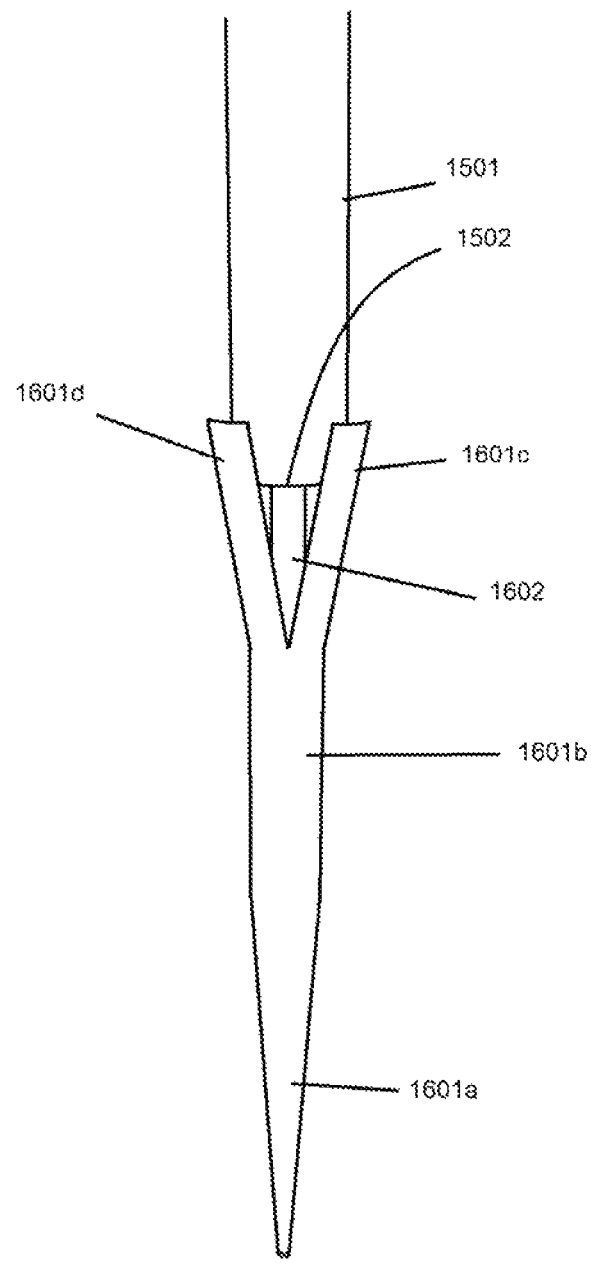
FIG. 8 shows a drainage tube and drainage tube introducer according to an embodiment of the present invention, with the drainage tube and the drainage tube introducer coupled together.
Figure 9:
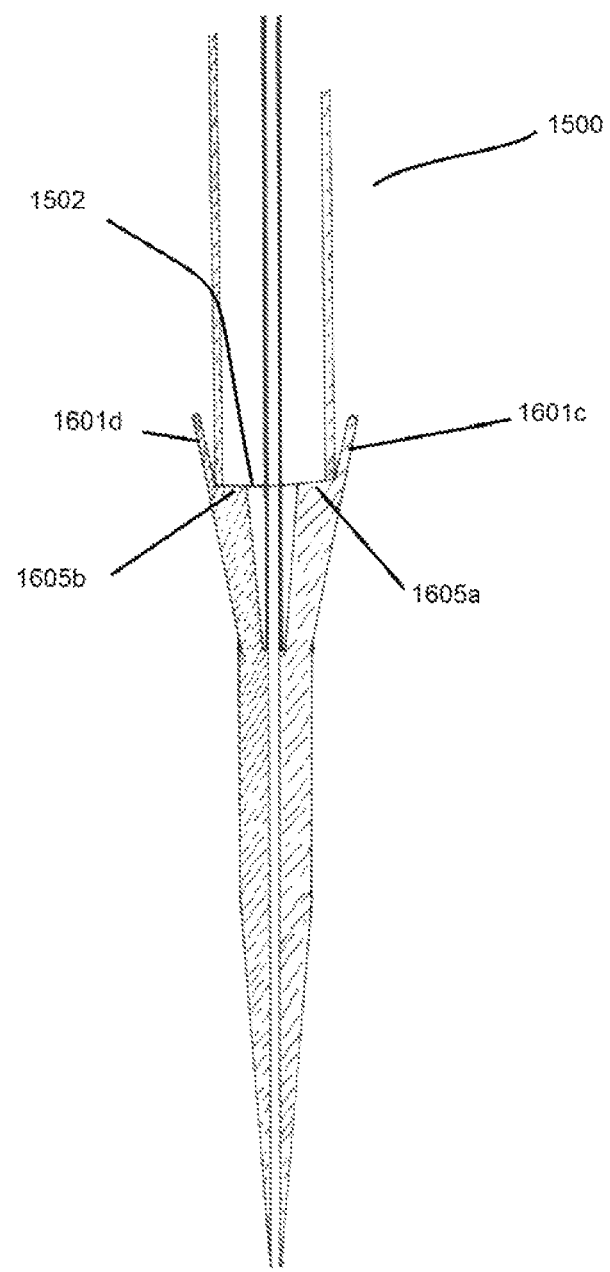
FIG. 9 shows a cross-sectional, close up view of a drainage tube and drainage tube introducer according to an embodiment of the present invention, with the drainage tube and the drainage tube introducer coupled together.

As shown in FIG. 7, the diameter of the drainage tube 1500 is greater than the diameter of the distal head 1601 of the introducer 1600. In order for the distal head 1601 to be engaged with the distal end 1502 of the drainage tube 1500, the retention clips must be stretched radially outward to accommodate the greater diameter of the drainage tube 1500, as shown in FIG. 8. Without limiting the invention, FIG. 9 shows a cross sectional view taken through the longitudinal axes of the drainage tube 1500 and the introducer 1600, which are shown engaged to one another. The interior surfaces of the retention clips 1601c and 1601d may contact the exterior diameter of the distal end 1502 of drainage tube 1500. Without limiting the invention, the retention clips 1601c and 1601d may include ridges 1605a and 1605b that abut the distal end 1502 of the drainage tube 1500 when the drainage tube is engaged with the retention clips 1601c and 1601d. The ridges 1605a and 1605b may also act as stops for the drainage tube 1500, defining the position of the distal end 1502 of the drainage tube 1500 when it is engaged with the introducer 1600. Without limiting the invention, the ridges 1605*a* and 1605*b* may be radially arranged walls having a thickness in a range of about 2 mm to about 10 mm, or any value or range of values therein (e.g., in the view in FIG. 9, the ridges are coplanar walls along the cross-sectional plane). In other implementations, the ridges may have a wider or circumferential structure, such as ridges that each run along the interior circumference of the retention clips 1601*c* and 1601*d* from slit to slit.

Further variations on the one or more surgical instruments described above are within the scope of the present invention, and the present invention is not limited to the specific examples and descriptions provided herein. Additionally, it is to be understood that the instruments and methods described herein may be used in combination with additional instruments and procedures.

Method of Use

Some embodiments of the present invention are drawn to novel methods of surgically accessing body cavities of a human or animal for various medical procedures. The methods described herein may utilize the one or more medical instruments described above, and may be used for various surgical procedures (e.g., laparoscopy; chest tube thoracostomy; introducing catheters for peritoneal dialysis, paracentesis, etc.; diagnostic peritoneal lavage; etc.) to establish an access incision into a body cavity with the novel surgical instruments described herein, which may allow the user (e.g., a surgeon or other medical personnel) to avoid damaging organs or tissues within the targeted cavity while at the same time not requiring general anesthesia or any additional equipment (e.g., camera, insufflation kit, fluoroscopy, etc.).

The novel instruments and methods of the present invention provide a safe and efficient means to establish access to a body cavity (e.g., in emergency situations) without sacrificing safety. The methods are minimally invasive, requiring only small incisions created by the safety needle and dilators, and only local anesthesia. Since general anesthesia is unnecessary, the methods of the present invention can be utilized without an operating room or interventional radiology suite. The procedures can be performed in the surgeon's office or in an examination room, and with little delay in emergency situations as in an emergency department or a trauma bay. This efficiency not only cuts down on the time and preparation required to perform the procedures, it also cuts down on the costs associating with the procedures, including costs for facilities, anesthesia, and additional equipment (e.g., camera, insufflation, fluoroscopy, etc.) or instruments. Additionally, because these procedures do not require general anesthesia or an operating room, the surgical instruments of the present invention can be used in a broader range of emergency situations and indications that can be addressed by the minimally invasive delivery of a catheter. For example, the surgical tools of the present invention may be used to establish a catheter for diagnostic peritoneal lavage or chest tube insertion in unstable patients.

In some embodiments, and without limitation, the presently disclosed surgical instruments may be used to establish access to the interior of a targeted cavity through a cannula that may allow the passage of various instruments into the targeted cavity (e.g., a laparoscopy procedure). In other embodiments, and without limitation, the presently disclosed surgical instruments may be used in methods that establish a catheter or tube accessing the interior of a targeted cavity with the purpose of draining gas or fluid from the interior of the targeted cavity. In some examples, and without limitation, the instruments and methods of the present application may be adapted to accessing the abdominal cavity for laparoscopic procedures, peritoneal dialysis, paracentesis in the case of liver failure or malignant ascites, among other applications. Other applications include establishing a catheter or drainage tube in the thoracic or abdominal cavity to drain pleural effusion or air, establishing a rigid or semi-rigid chest tube in the thoracic cavity to drain viscous fluids (e.g., blood and/or puss, etc.), establishing a catheter for diagnostic peritoneal lavage, etc. Further applications of the surgical instruments of the present invention may include establishing a shunt in a body cavity, such as ventriculoperitoneal shunt. Additional methods and uses for the instruments described herein are within the scope of the present invention, as well.

Figure 10:
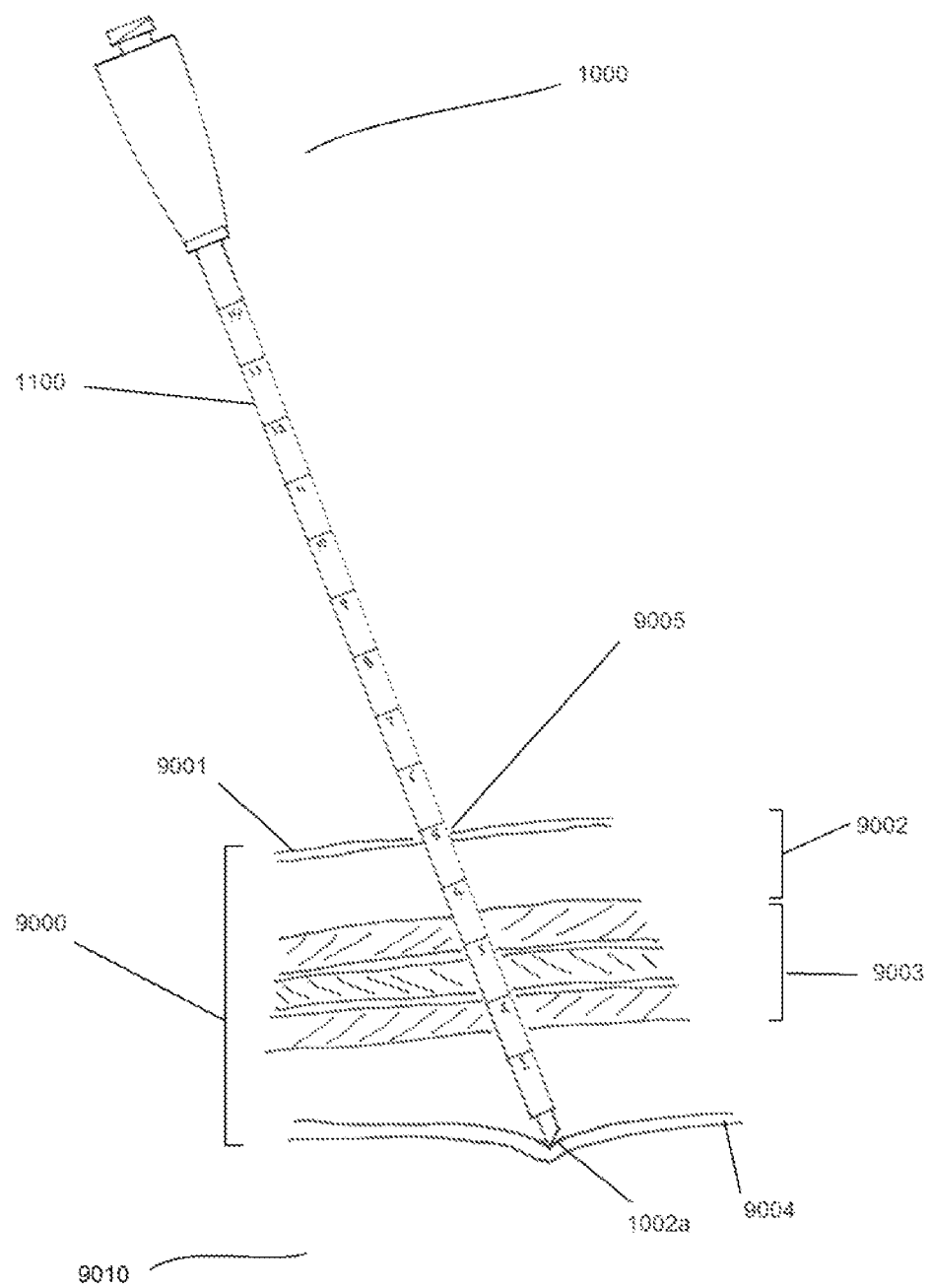
FIG. 10 shows a step of advancing a coupled safety needle and flexible sheath assembly being advanced through the wall of a targeted body cavity according to an embodiment of the present invention.
Figure 11:
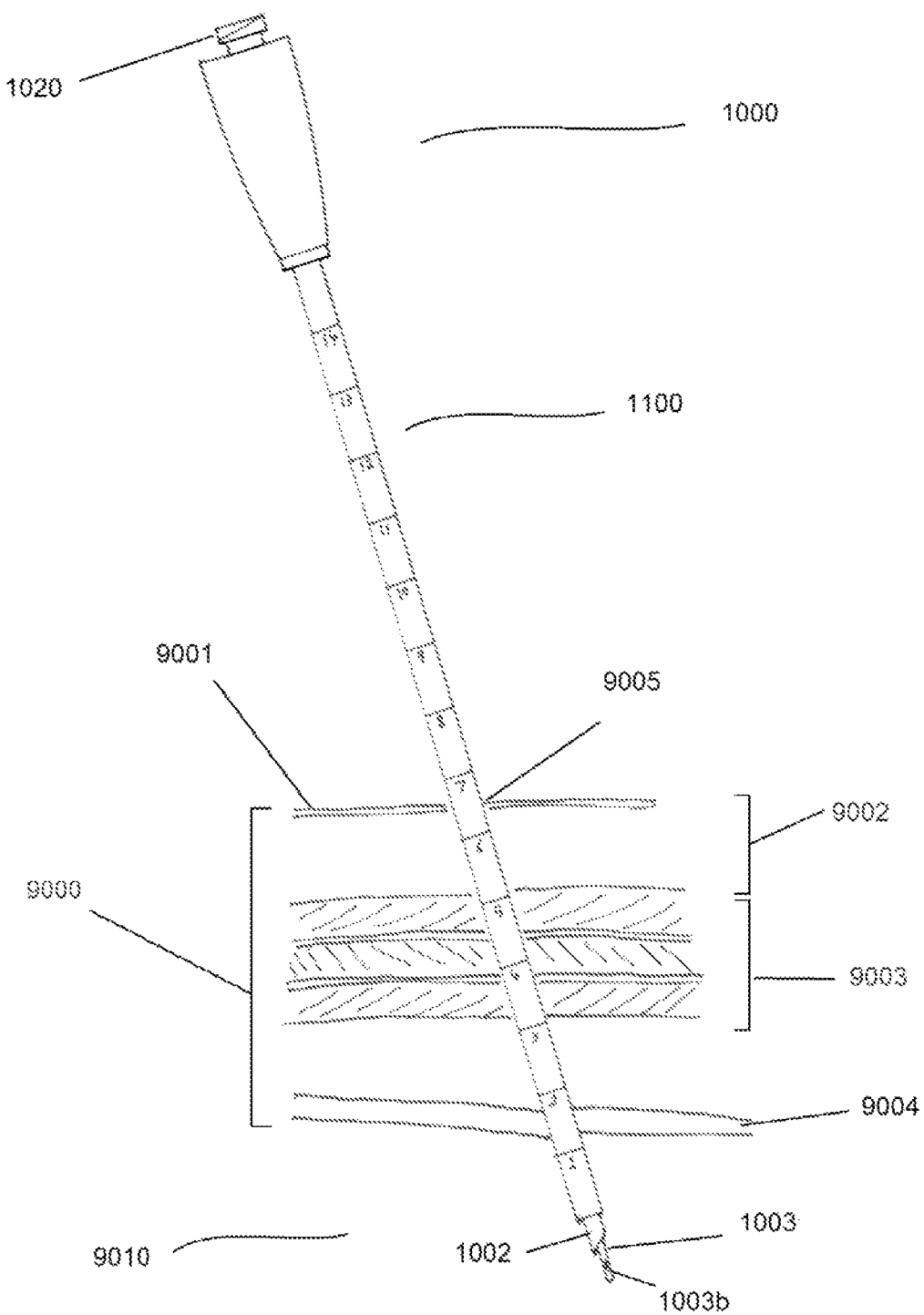
FIG. 11 shows a coupled safety needle and flexible sheath assembly advanced into a targeted body cavity according to an embodiment of the present invention.

Without limiting the invention, FIG. 10 shows the coupled safety needle 1000 and the flexible sheath 1100 being advanced through a cavity wall 9000 (e.g., an abdominal cavity wall, a thoracic cavity wall, etc.). As can be seen from FIG. 10, the safety needle 1000 is advanced at an oblique angle (e.g., in a range of about 10° to about 45° from the normal or imaginary line perpendicular to the surface of the skin, or any angle or range of angles therein) relative to the surface of the skin 9001, with the distal-most edge of the sharpened cutting edge 1002*a* leading the needle through the incision 9005. As the safety needle is advanced by the user into the cavity wall 9000, the blunt stylet 1003 is pressed by the contact with the cavity wall into the sharp outer cannula 1002 of the safety needle 1000. The safety needle 1000 and the flexible sheath 1100 are successively advanced through the skin 9001, the adipose and connective tissues 9002, the muscle tissue 9003, and then the membrane lining the body cavity (e.g., the peritoneum, pleural membrane, etc.). As shown in FIG. 10, the blunt stylet 1003 may remain within the sharp outer cannula 1002 until the safety needle advances through the membrane 9004.

In some implementations, the user may employ a safety needle that has a tension adjustment system (e.g., similar to the safety needle shown in FIG. 4), and may employ the extra step of selecting a specific spring tension setting to accommodate the tensile strength of the cavity wall and the physical condition of the patient (e.g., muscle tone, fat tissue, etc.).

Once the safety needle has sufficiently penetrated the cavity wall 9000, including the membrane 9004 lining the cavity wall, the pressure applied by the tissues of the cavity wall 9000 are removed, and the blunt stylet 1003 may protrude from the sharp outer cannula 1002, movement of the blunt stylet 1003 within the safety needle that may trigger audible and/or visual indicators that inform the user that the blunt stylet 1003 has extended and the safety needle has penetrated the targeted cavity 9010. The visual indicator may be a mechanical color indicator that is activated by the stylet spring 1020 within the safety needle 1000. For instance, the color indicator may be a colored cylinder (e.g., having a red band and green band, not shown) that is aligned with a clear slot (not shown) in the side of the safety needle 1000, and the cylinder may move up and down the with respect to the clear slot as the blunt stylet 1003 is moved in and out of the sharp outer cannula 1002. The audible indicator may a click that results from the proximal end of the blunt stylet (e.g., a lip or flange) contacting a lip, rim, or other structure within the safety needle 1000.

With the safety needle 1000 and the flexible outer sheath 1100 in place within the targeted cavity 9010, the cavity (e.g., the peritoneal cavity) may be insufflated with a gas (e.g., $CO_2$) to create space between the cavity wall 9000 (and, optionally, membranes lining the cavity wall) and the organs lying therein. The insufflating gas may be passed through the safety needle 1000, specifically the blunt stylet 1003, which may include a gas passage that runs from the connector 1050 (e.g., a threaded connector) at the proximal end of the safety needle to the gas port 1003*b* near the distal blunt tip 1003*a* for allowing the insufflation gas to pass into the cavity. Alternatively or additionally, insufflation of the targeted cavity may later be accomplished through the flexible sheath. The insufflation gas may be provided from a gas source, through a gas line (which may include a stop cock or other flow control mechanism) that may be attached to the connector 1050 at the proximal end of the safety needle 1000. In other implementations, insufflation may not be performed after the safety needle 1000 and flexible sheath have been introduced into a targeted cavity. For example, in the case of a procedure to establish an access incision in the thoracic cavity or in the abdomen when placing a peritoneal catheter for dialysis, paracentesis or diagnostic peritoneal lavage, insufflation would not be used.

When the tip of the safety needle enters the cavity, the visual or audible indicator(s) may notify the surgeon and/or other medical personnel that the safety needle is in the proper position. Subsequently, the surgeon or other medical personnel may hold the safety needle steady to prevent advancement or movement of the needle (e.g., the surgeon or other medical personnel hold the safety needle as his hand is resting on the body of the patient). Subsequently, the safety needle 1000 may be disengaged from the flexible sheath 1100 at the connectors 1010 and 1102, and the flexible sheath may be advanced into the targeted cavity 9010 while the safety needle is held in place (e.g., by the surgeon's other hand). The surgeon or other medical personnel should stop advancing the flexible sheath when the marking 1060 on the safety needle 1000 is exposed by the advancement of the sheath 1100 into the cavity, thereby indicating that the tip of the flexible sheath is within the cavity. At that point, the surgeon or other medical personnel may note the depth marking on the flexible sheath at the level of the skin 1104. The surgeon or other medical personnel may later use the noted depth marking to help insert the cannula/dilator to the same level. The desired depth of the flexible sheath 1100 may depend on the size of the patient and the cavity into which the flexible sheath 1100 has been placed. For example, an without limitation, if the sheath has been established in an insufflated abdominal cavity, the user may need to advance the flexible sheath to a greater depth than if the flexible sheath was established in a more caudal area, such as the pelvic cavity.

Figure 13:
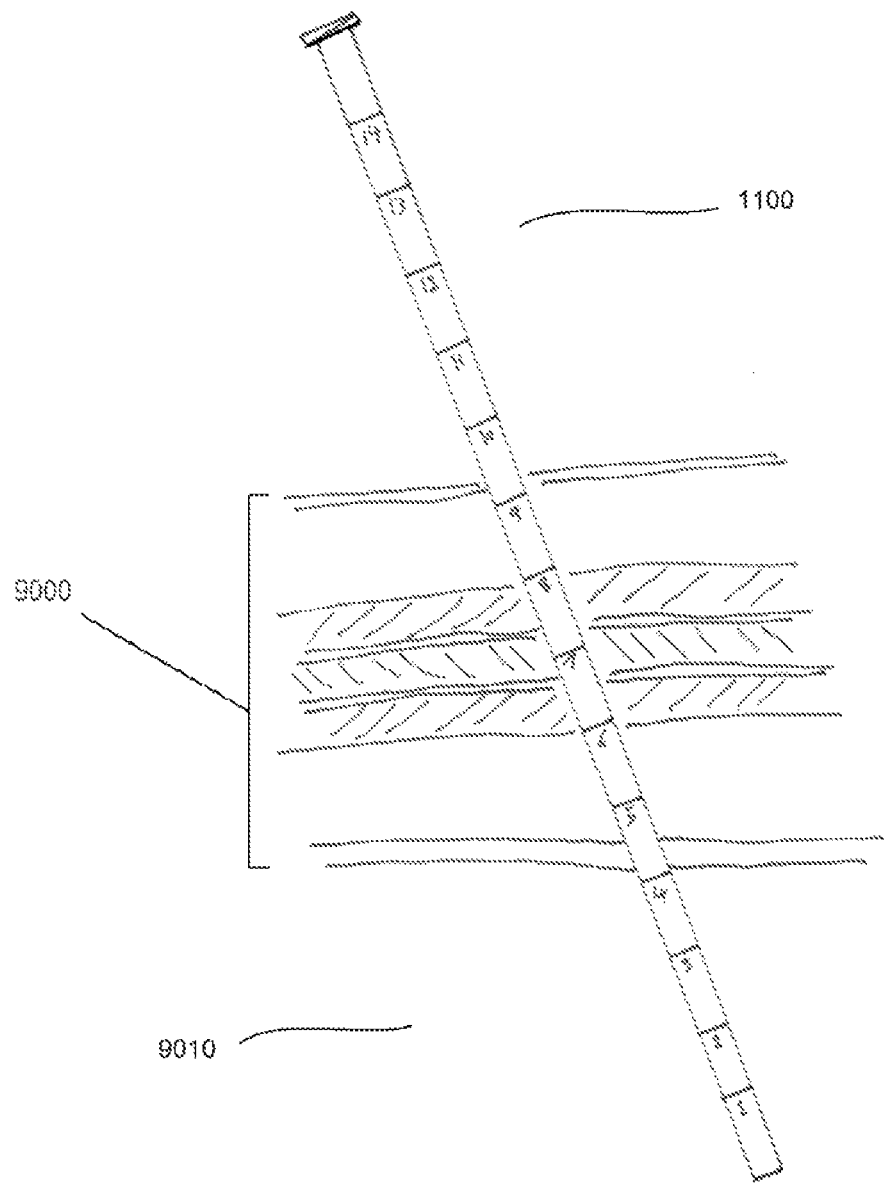
FIG. 13 shows a flexible sheath having its distal end placed into a targeted body cavity according to an embodiment of the present invention.

The example shown in FIG. 13 shows the flexible sheath 1100 advanced to a depth of about 9.5 units (e.g., centimeters). The user may advance the flexible sheath 1100 into the targeted cavity 9000 without fear of damaging tissues or organs because of the flexible construction of the flexible sheath 1100.

Once the flexible sheath 1100 is established at a desired depth, the safety needle may be removed from the flexible sheath 1100 and the targeted body cavity 9010 to leave the flexible sheath 1100 established within the cavity 9000, as shown in FIG. 13. In some implementations, the flexible sheath 1100 may be utilized to determine a safe depth to which other instruments (e.g., the dilator 1300 and cannula 1400) may be advanced into the access incision 9005. For example, an endoscope may be advanced through the flexible sheath 1100 to determine whether the flexible sheath 1100 has been advanced to the point that it is in contact with the organs within the cavity, and, if not, how close the flexible sheath 1100 is to the organs. If the flexible sheath 1100 is at a safe depth, the user can then use that depth as a guide. If flexible sheath is too close to or too far from the targeted organs or tissues, the user may adjust the depth of the flexible sheath accordingly.

Figure 14:
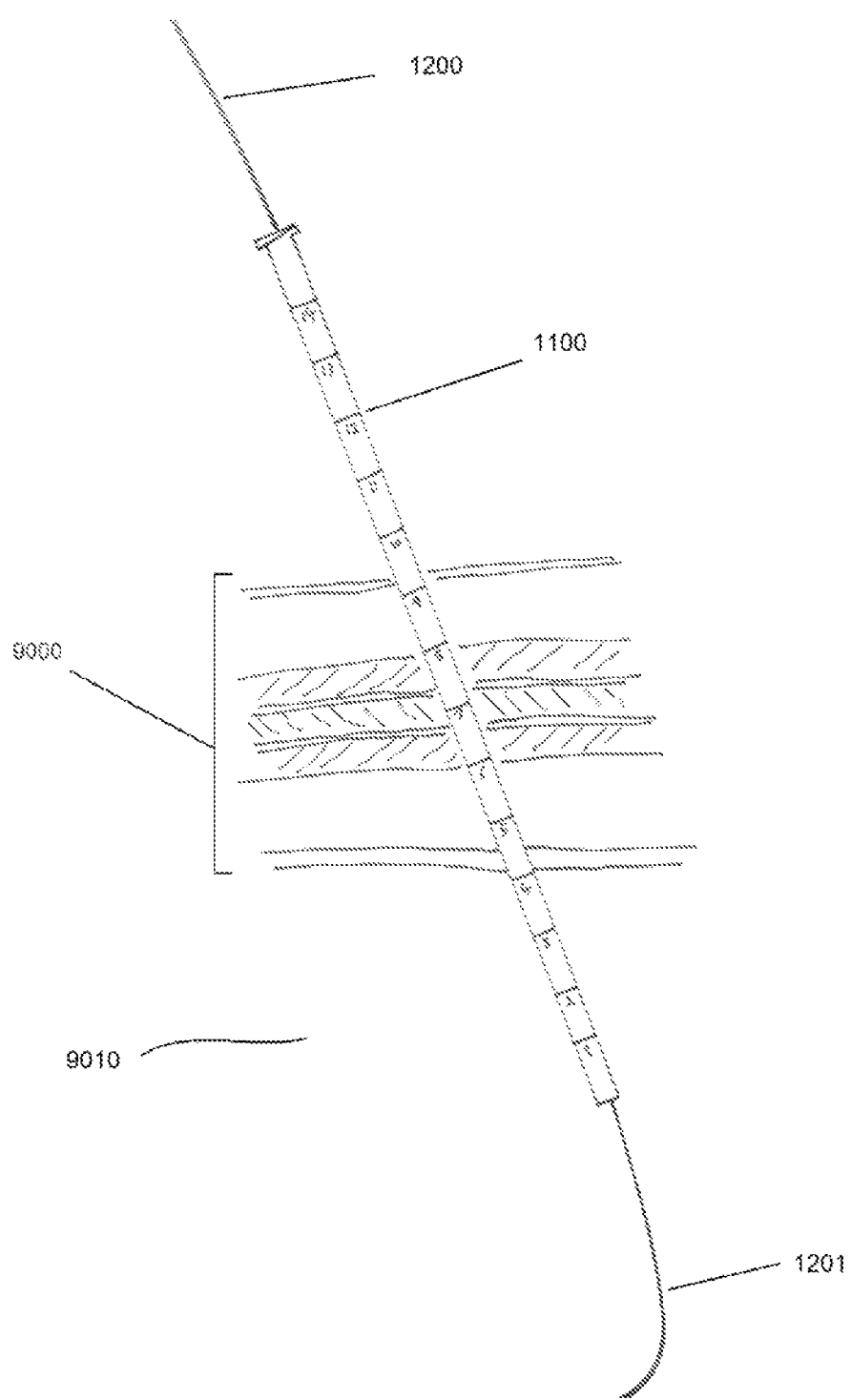
FIG. 14 shows a step of advancing a guide wire through a flexible sheath and into a targeted body cavity according to an embodiment of the present invention.

As shown in FIG. 14, with the safety needle 1000 removed, a guide wire 1200 may be threaded through the flexible sheath 1100 and advanced into the targeted cavity 9010. The guide wire 1200 may have graduation markings thereon to allow the user to discern the depth to which the guide wire may be advanced into the targeted cavity 9010. The guide wire may be advanced to a predetermined depth through the flexible sheath 1100 (e.g., to a 20 cm marker on the wire) to ensure that the tip of the wire reaches the targeted cavity. The guide wire 1200 may include a flexible curved tip wire at its end to prevent possible injuries from straight-tip wires 9005. The guide wire 1200 may be established in the access incision 9005 to guide additional instruments through incision.

Figure 15:
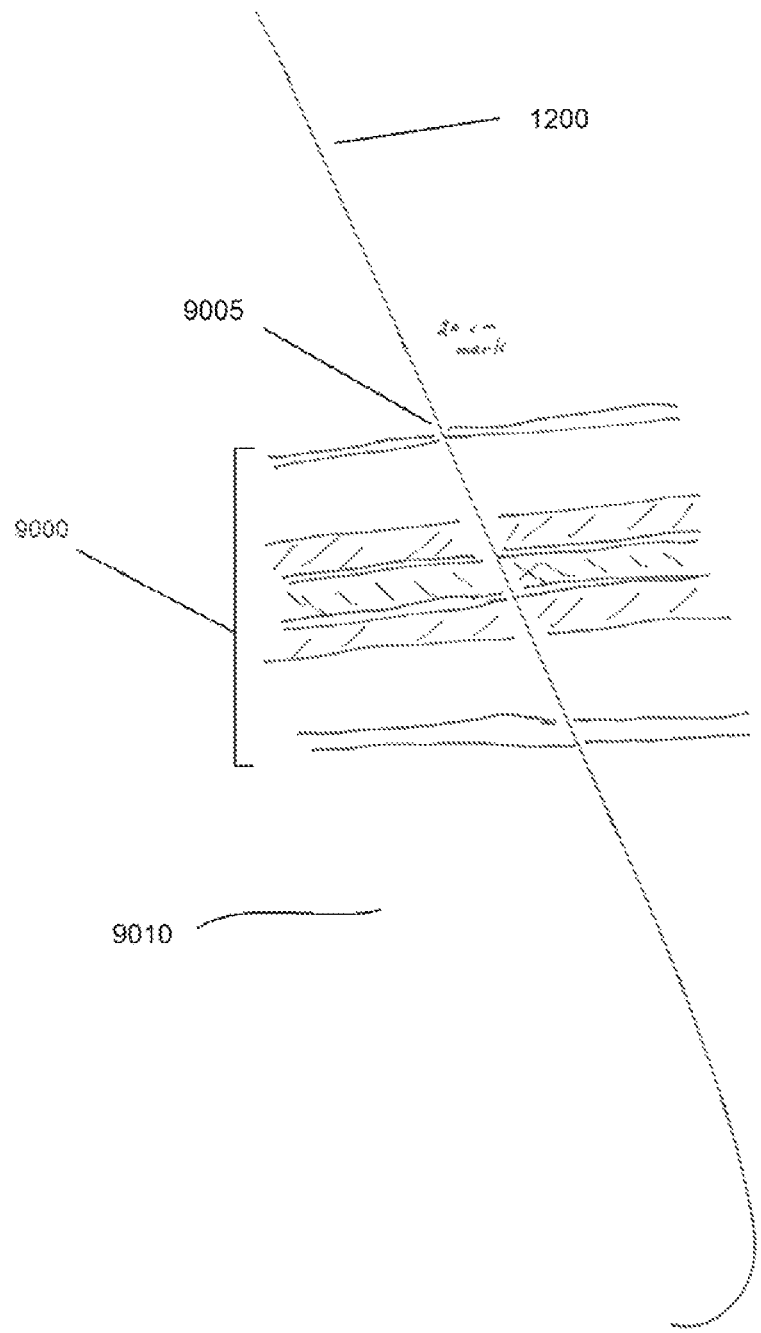
FIG. 15 shows a guide wire established through an access incision and within a targeted body cavity according to an embodiment of the present invention.

As shown in FIG. 15, once the guide wire 1200 is established in the targeted cavity 9010, the flexible sheath 1100 may be removed from the targeted cavity 9010 through the access incision 9005. Once the flexible sheath 1100 is removed from the cavity, the dilator and cannula system may be advanced through the access incision in order to establish an access port into the targeted cavity.

Figure 16:
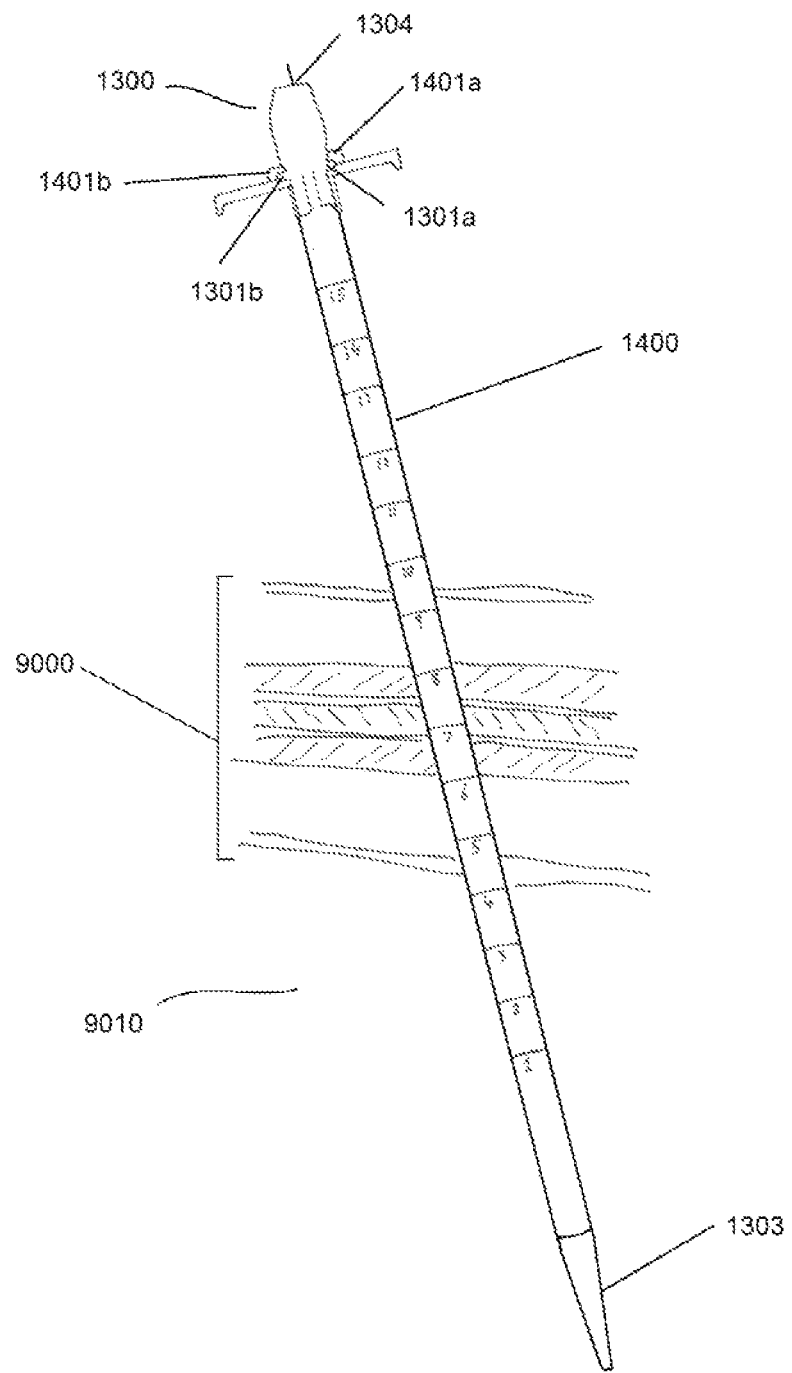
FIG. 16 shows a step of advancing a split sheath and dilator assembly over a guide wire and into a targeted body cavity according to an embodiment of the present invention.

As shown in FIG. 16, the dilator 1300 and the cannula 1400 may be coupled together and advanced over the guide wire 1200 and into the targeted cavity 9010, thereby dilating the access incision 9005 and establishing an access port through the cannula 1400. Prior to insertion into the access incision 9005, the dilator 1300 may be inserted into the cannula 1400 through the proximal end of the cannula 1400, and may then be locked into position in the cannula 1400 by engaging locking tabs 1301*a* and 1301*b* with locking notches 1401*a* and 1401*b*, respectively. The proximal end of the guide wire 1200 may then be threaded through the central canal 1304 of the dilator 1300, and the dilator-cannula combination may be then be advanced by the user through the access incision 9005. The cannula 1400 may have graduation markings 1402*a* on its exterior allowing the user to determine the depth to which the cannula 1400 and the coupled dilator 1300 are advanced into the targeted cavity 9010. For example, FIG. 16 shows that the cannula 1400 may be advanced to the same depth (9.5 units) to which the flexible sheath has been advanced (e.g., to ensure that the cannula reaches into the cavity).

Figure 17:
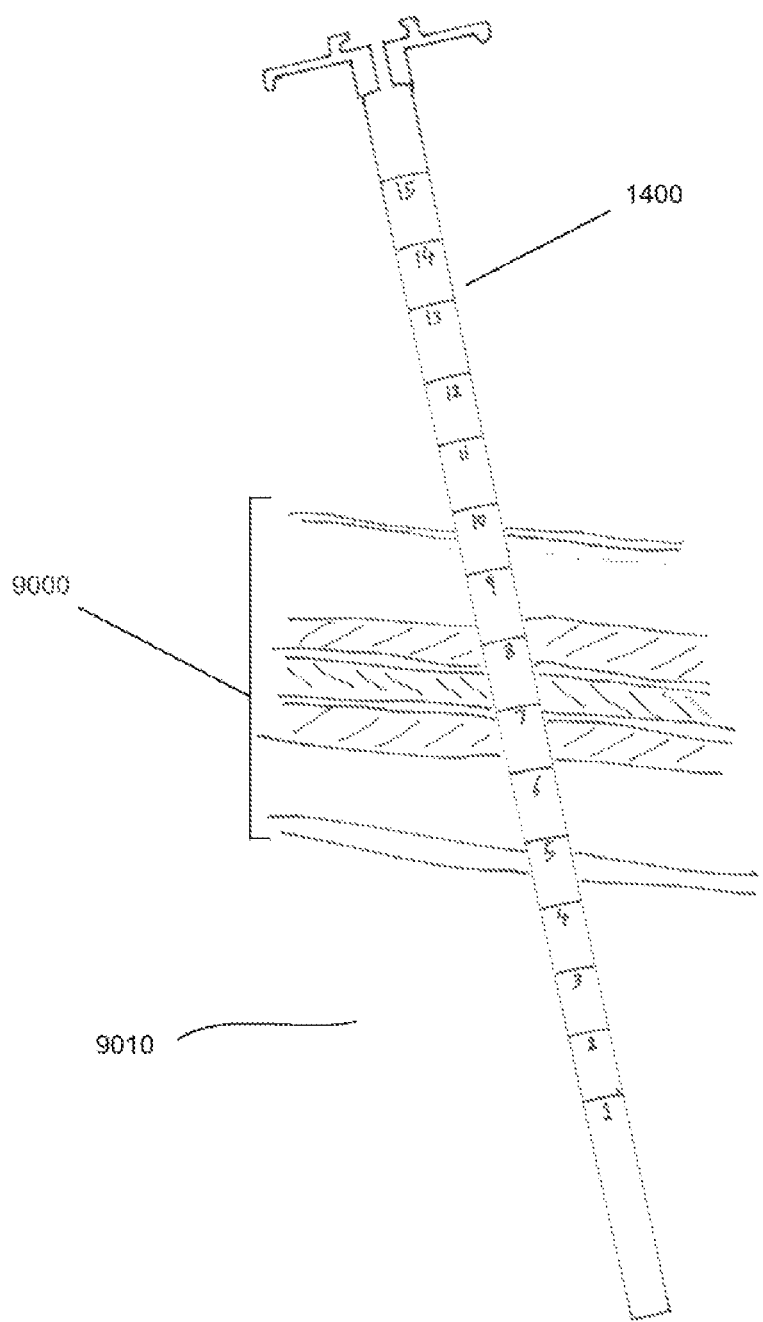
FIG. 17 shows a split sheath having its distal end placed into a targeted body cavity according to an embodiment of the present invention.

As shown in FIG. 17, once the cannula 1400 is established at the desired depth, the dilator 1300 can be disengaged from the cannula 1400 (the locking tabs 1301*a* and 1301*b* may be uncoupled from the locking notches 1401*a* and 1401*b*, respectively) and the dilator 1300 may be removed along with the wire from the targeted cavity 9010 and the cannula 1400. In other implementations, the position of the cannula 1400 may be manipulated or changed after the dilator 1300 is removed from the cannula 1400. This may be beneficial because the dilator may have a portion that extends multiple centimeters beyond the end of the cannula (e.g., in a range of about 2 to about 4 centimeters, or value or range of values therein). In such implementations, the user may wait to advance the cannula 1400 to the desired depth until after the dilator 1300 has been removed.

Once the cannula 1400 is established in the targeted cavity, e.g., as shown in FIG. 17, various additional surgical tools (e.g., forceps, endoscope, etc.) may be advanced through the access port provided by the cannula 1400. The access port may be utilized to place a flexible catheter through it. That catheter may be a peritoneal dialysis catheter, a paracentesis catheter, diagnostic peritoneal lavage catheter, a ventriculoperitoneal shunt catheter, a pleural catheter, or other catheter structures. In other embodiments, and without limitation, the cannula may be placed in the abdominal cavity to drain the ascitic fluid, in addition to or rather than providing a port for additional instruments. In further embodiments, and without limitation, in an emergency diagnostic peritoneal lavage, the catheter may be placed in the abdominal cavity to aspirate fluid through the cannula (e.g., using a syringe), and if no blood is detected, saline may be infused through the cannula and then drained for lab analysis. In addition, the kit may be used in various surgical procedures (e.g., laparoscopic cholecystectomy, laparoscopic hysterectomy, laparoscopic appendectomy, etc.). It is to be understood, that the scope of the present invention includes method of using the surgical instruments of the present invention in further situations (e.g., emergency situations), and that the invention is not limited to the specific examples provided herein.

In further embodiments, and without limitation, the presently disclosed surgical instruments may be used in methods that establish a tube or catheter accessing the interior of a targeted cavity with the purpose of draining gas or fluid from the interior of the targeted cavity (e.g., a chest tube thoracostomy procedure, a drainage tube in the case of diagnostic peritoneal lavage, etc.). As an example, and without limitation, FIGS. 18-25 show a process that differs from the previous discussed methods from the point of establishing a guide wire 1200 within the targeted cavity 9010 (e.g., as shown in FIG. 15). The exemplary process shown in FIGS. 18-25 establishes a drainage tube in targeted cavity 9010.

Figure 18:
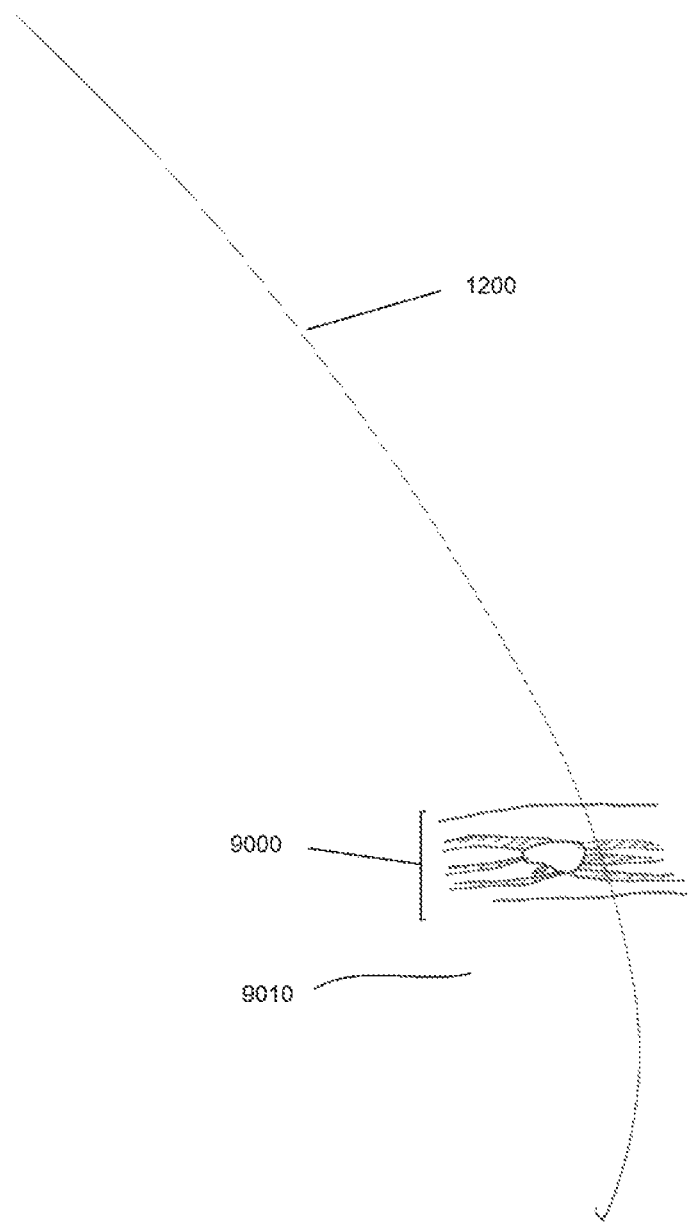
FIG. 18 shows a guide wire established through an access incision and within a targeted body cavity according to an embodiment of the present invention.

As previously discussed, the coupled safety needle and flexible sheath may be used to establish a guide wire 1200 in the targeted cavity 9010 (see, e.g., FIG. 18). Once the guide wire 1200 is established in the targeted cavity 9010, the drainage tube 1500 and the drainage tube introducer 1600 maybe coupled to each other as previously described (see, e.g., the discussion of FIGS. 8-9 above) and proximal end of the guide wire 1200 may be threaded through the central guide wire canal 1603 of the introducer 1600. The guide wire 1200 may have one or more length or graduation markers thereon (see, e.g., FIG. 15) for determined the depth to which the drainage tube introducer has been advanced into the targeted cavity, allowing the surgeon or other medical personnel to control the depth to which the introducer is inserted. For example, and without limitation, the guide wire may have a single length marker that marks a max depth for insertion of a drainage tube or catheter into the cavity over the guide wire.

Figure 19:
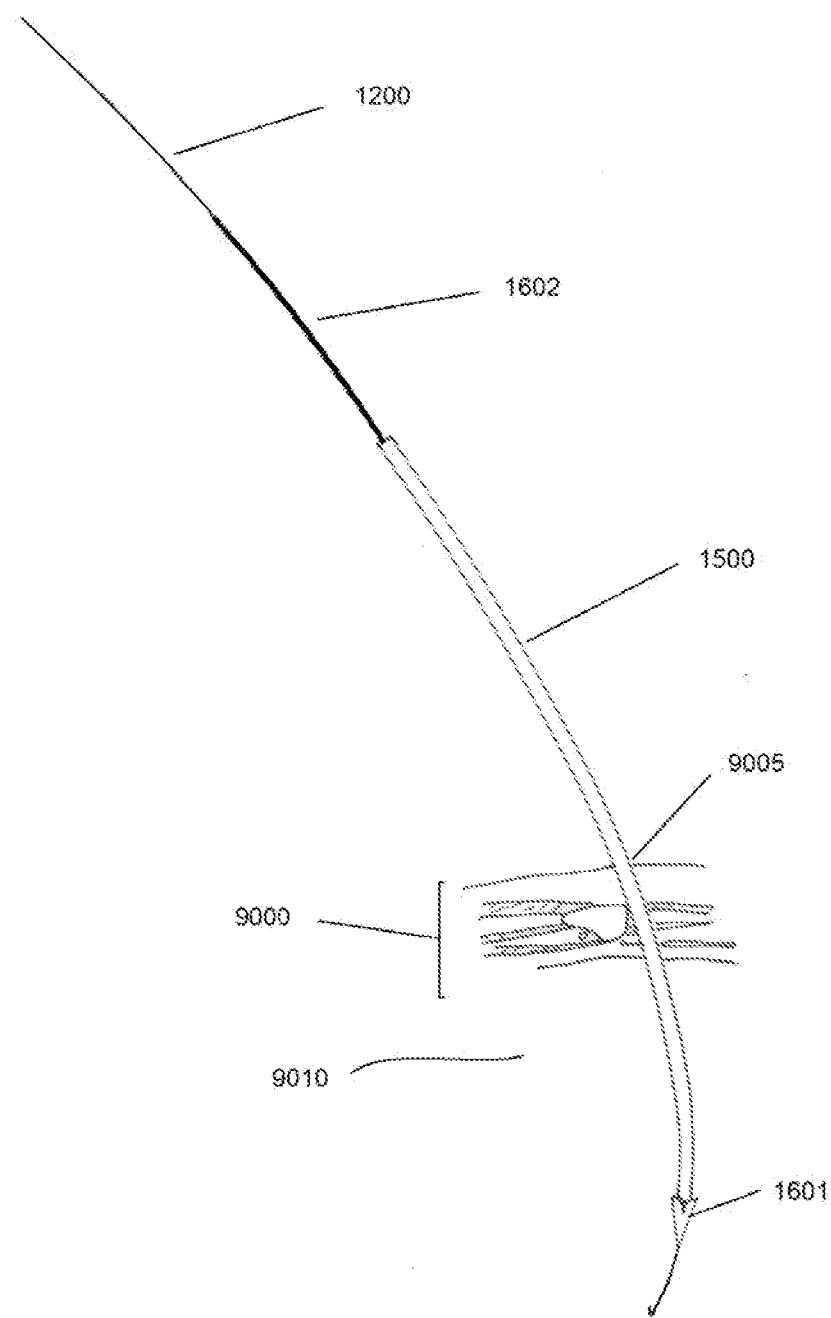
FIG. 19 shows a step of advancing a drainage tube and drainage tube introducer assembly over a guide wire and into a targeted body cavity according to an embodiment of the present invention.

As shown in FIG. 19, the coupled drainage tube 1500 and introducer 1600 may be advanced along the guide wire 1200 and through the access incision 9005 to both dilate the access incision 9005 and establish the drainage tube 1500 in the targeted cavity 9010. The expanded distal head 1601 of the introducer 1600 has a tapered profile that may be effective to dilate the access incision as the user advances the coupled drainage tube 1500 and introducer 1600 on the wire 1200 through the cavity wall 9000.

Figure 20:
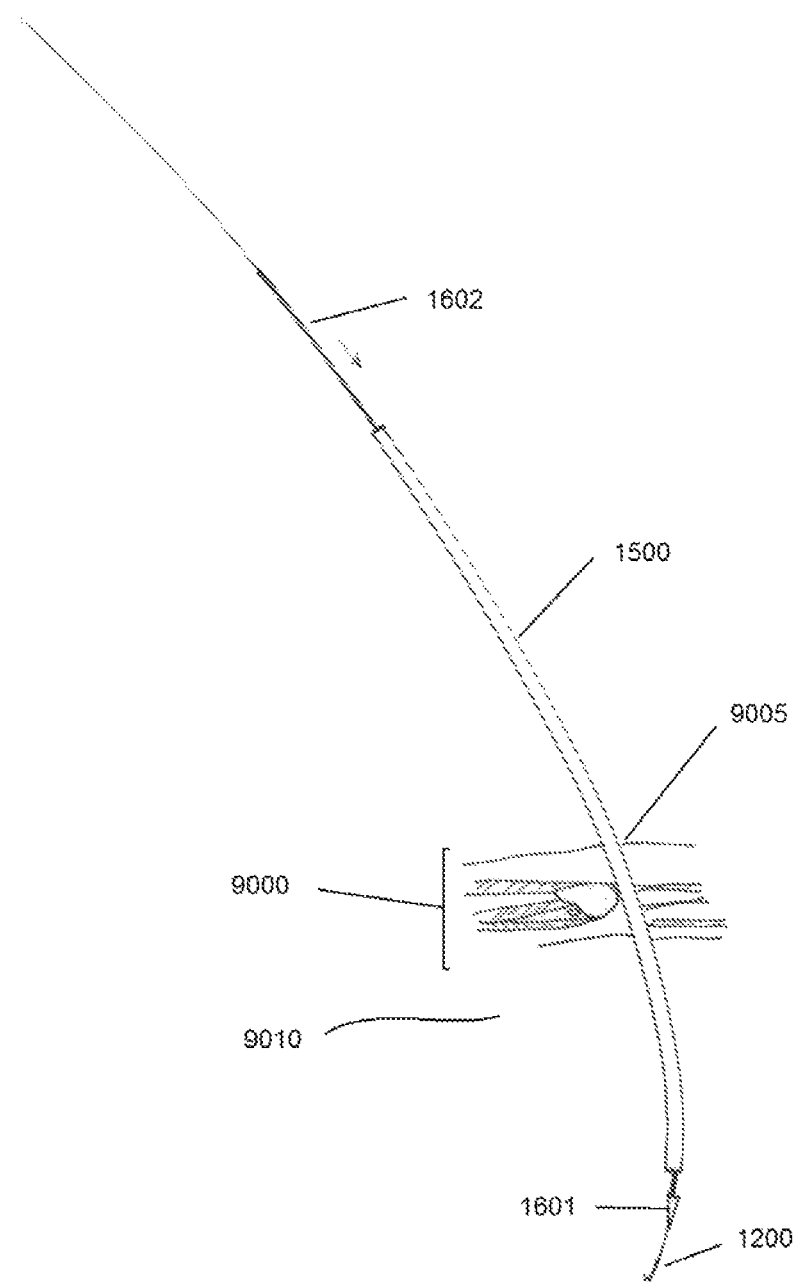
FIG. 20 shows a step of disengaging a drainage tube from a drainage tube introducer according to an embodiment of the present invention.
Figure 21:
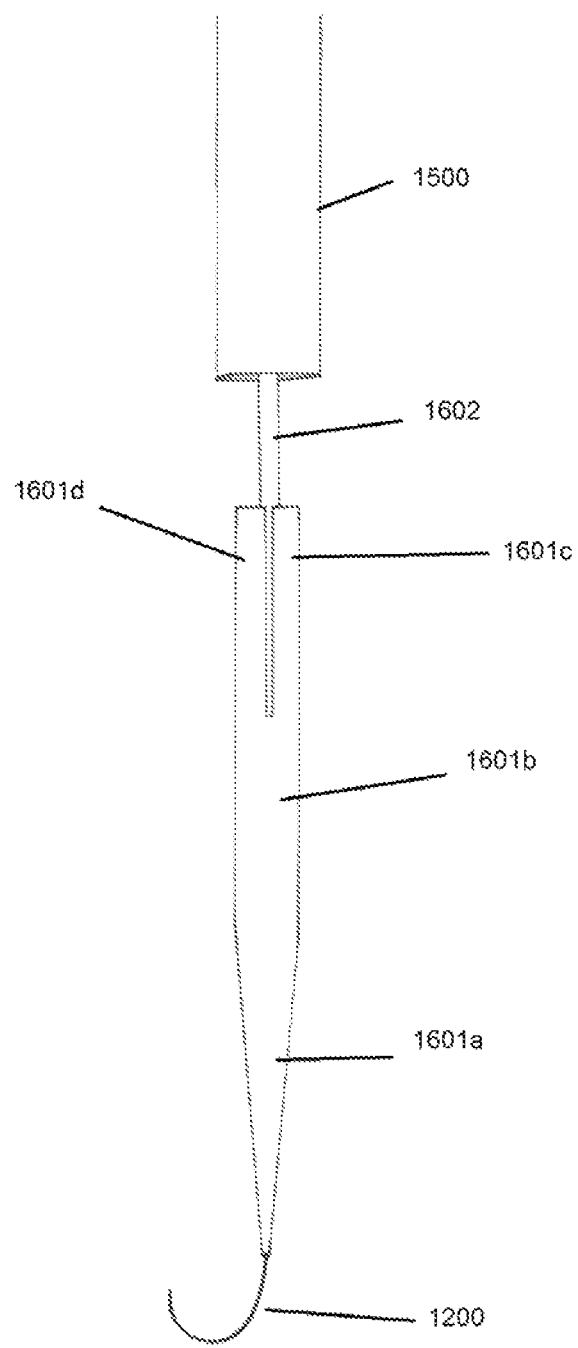
FIG. 21 shows a close-up view of a drainage tube introducer disengaged from a distal end of a drainage tube according to an embodiment of the present invention.
Figure 22:
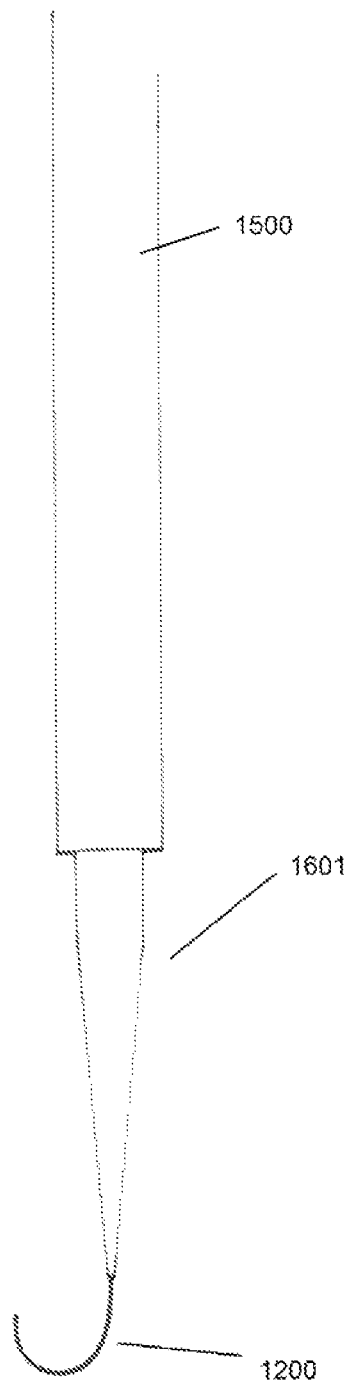
FIG. 22 shows a close-up view of a step of drawing a drainage tube introducer proximally through a drainage tube according to an embodiment of the present invention.

Once the drainage tube 1500 is established in the targeted cavity 9010, the distal head 1601 (the retention clips 1601*c* and 1601*d*) may be disengaged from the distal end of the drainage tube 1500, so that the introducer 1600 may be removed from the targeted cavity 9010. FIG. 20 shows how the introducer 1600 may be advanced further into the targeted cavity 9010 as the drainage tube 1500 is held stationary in order to disengage the distal head 1601 from the distal end of the drainage tube 1500. FIG. 21 shows an up-close view of the distal head 1601 after it has been disengaged from the distal end of the drainage tube 1500. The guide wire tube 1602 of the introducer 1600 may be a relatively stiff or rigid material (e.g., a rigid plastic) such that the distal head 1601 can be disengaged from the distal end 1502 of the drainage tube by pushing the guide wire tube 1602 distally through the drainage tube 1500. The retention clips 1601*c* and 1601*d* resile to their original position such that the largest diameter of the distal head 1601 is narrower than the diameter of the drainage tube 1500. As shown in FIG. 22, the relatively small diameter of the distal head 1601 allows it to be pulled through the drainage 1500 and back out of the targeted cavity 9010.

Figure 23:
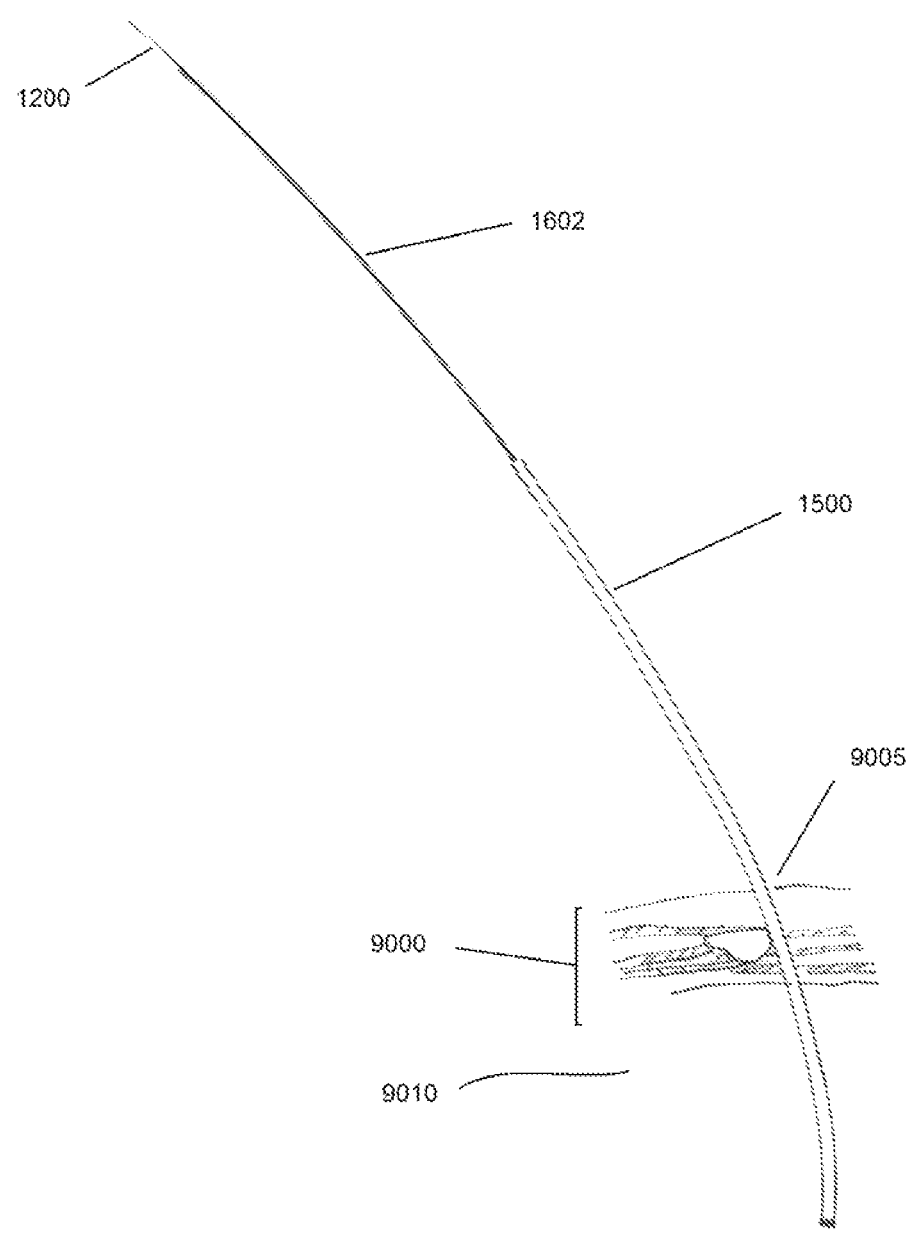
FIG. 23 shows a step of drawing a drainage tube introducer proximally through a drainage tube according to an embodiment of the present invention.
Figure 24:
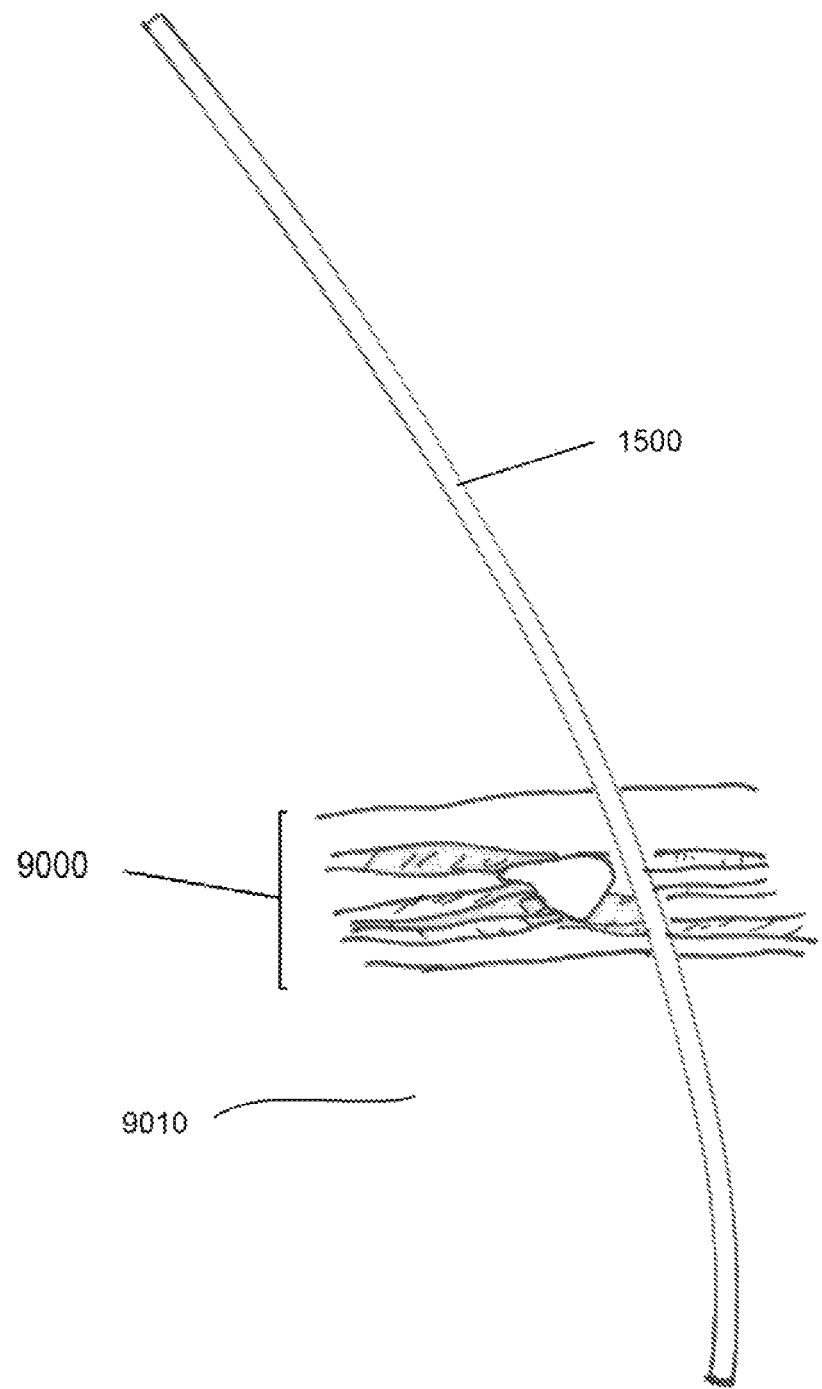
FIG. 24 shows a drainage tube established through an access incision and within a targeted body cavity according to an embodiment of the present invention.

FIG. 23 shows an example of the removal of the introducer 1600 along with the wire 1200 through the drainage tube 1500. The length of the guide wire tube 1602 may be longer than the drainage tube 1500 such that it can be used to grip and remove the introducer 1600 through the drainage tube 1500. The guide wire 1200 may also assist in removing the introducer 1600. As shown in FIG. 24, once the introducer 1600 is removed from the targeted cavity 9010 through the drainage tube 1500, the drainage tube 1500 can function to drain gas or fluid within the targeted cavity, thereby relieving pressure on the organs therein.

This procedure is particularly useful for emergency situations in which there is insufficient time to prepare an operating room to treat the patient (e.g., the patient has hemothorax or empyema). The drainage tube introducer method can be used to quickly establish a chest tube in the thoracic cavity while preventing intrathoracic injury to the lungs and other tissues therein or to establish a drainage tube in the abdominal cavity for diagnostic peritoneal lavage while preventing intra-abdominal injury to the organs and tissues therein. A heavier or stiffer and higher gauge drainage may be used to facilitate the flow of more viscous fluid (e.g., in the case of hemothorax, empyema, etc.). Where drainage of a low viscosity fluid or a gas may be needed (e.g., for pleural effusion or air in the thorax), a softer and smaller gauge drainage tube may be used. These procedures can be performed quickly and safely without general anesthesia. Thus, a patient with a life threatening condition (e.g., hemothorax) can be efficiently treated. This method may avoid the inherent risks associated with traditional methods. In addition, it minimizes tissue trauma that results in less pain and less risk of bleeding/injuries.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed:

1. A medical instrument kit for establishing an access port in a targeted body cavity without damaging the organs or tissues therein, comprising:
    a. a safety needle assembly having an outer cannula having an exterior diameter and a distal cutting end, and an inner stylet having a blunt distal end, wherein the stylet is spring biased to extend from said distal cutting end with sufficient pressure to protrude from said distal cutting end when said distal cutting end penetrates into an interior space of said targeted body cavity;

b. a flexible hollow sheath for coupling with said safety needle, wherein said flexible sheath is positioned over said outer cannula and said flexible sheath has an inner diameter that is substantially equal to said outer diameter of said outer cannula and fits snuogly over said outer cannula;

c. a drainage tube; and d. a drainage tube introducer including a distal head for engaging a distal end of said drainage tube and dilating an access incision to allow said drainage tube to pass into said targeted body cavity, wherein said distal head includes two resilient clips for engaging and holding a distal end of said drainage tube, said clip being stretched from a first resting position to a second radially stretched position to sit over an outer diameter of the drainage tube thereby increasing a diameter of the distal head from an original diameter to a stretched diameter.

2. The kit of claim 1, wherein said kit further includes a guide wire for guiding said drainage tube introducer and said drainage tube into said targeted body cavity, said guide wire having at least one graduation marking thereon.

3. The kit of claim 2, wherein said drainage tube introducer includes a central guide wire canal for receiving said guide wire.

4. The kit of claim 1, wherein said resilient clips resile to their first position when they are disengaged from the drainage tube, thereby returning the distal head to said original diameter.

5. The kit of claims 4, wherein said original diameter of the distal head is less than the smallest diameter of said drainage tube, allowing said drainage tube introducer to pass through said drainage tube.

6. The kit of claim 1, wherein said safety needle assembly further includes a first connector and said flexible sheath comprises a second connector, said first and second connectors being to mechanically couple said safety needle to said flexible sheath.

7. The kit of claim 1, further comprising a tension adjustment system for adjusting the force applied to the inner stylet by a biasing structure.

8. The kit of claim 7, wherein said biasing structure is a spring and said tension adjustment system includes multiple discrete tension settings for changing an amount of force applied by said spring to said inner stylet.

9. The kit of claim 1, wherein said safety needle is operable to be reversibly inserted into said flexible hollow sheath to pair said safety needle and said flexible hollow sheath, and said paired safety needle and said flexible hollow sheath are operable to penetrate through a cavity wall of a patient and establish the flexible hollow sheath in said cavity wall to expose the interior of said cavity.

10. A medical instrument kit for establishing an access port in a targeted body cavity without damaging the organs or tissues therein, comprising:

a. a safety needle assembly having an outer cannula with distal cutting end and an inner stylet having a blunt distal end that retractably protrudes from said distal cutting end, said safety assembly being operable to penetrate through a body cavity wall of a patient;

b. a drainage tube; and c. a drainage tube introducer including a distal head for engaging a distal end of said drainage tube and dilating said access incision to allow said drainage tube to pass into said targeted body cavity, wherein said drainage tube introducer is operable to be retracted through said drainage tube after said drainage tube is passed into said targeted body cavity, wherein said distal head includes two resilient clips for engaging and holding the distal end of said drainage tube, said clip being stretched from a first resting position to a second radially stretched position to sit over an outer diameter of the drainage tube thereby increasing a diameter of the distal head from an original diameter to a stretched diameter.

11. The kit of claim 10, further comprising a flexible hollow sheath for coupling with said safety needle, wherein said flexible sheath is positioned over said outer cannula and said flexible sheath has an inner diameter that is substantially equal to an outer diameter of said outer cannula and fits snuggly over said outer cannula.

12. The kit of claim 11, wherein said safety needle is operable to be reversibly inserted into said flexible hollow sheath to pair said safety needle and said flexible hollow sheath, and said paired safety needle and said flexible hollow sheath are operable to penetrate through a cavity wall of a patient and establish the flexible hollow sheath in said cavity wall to expose the interior of said cavity.

13. The kit of claim 10, wherein said kit further includes a guide wire for guiding said drainage tube introducer and said drainage tube into said targeted body cavity, said guide wire having at least one graduation marking thereon.

14. The kit of claim 13, wherein said drainage tube introducer includes a central guide wire canal for receiving said guide wire.

15. The kit of claim 10, wherein said resilient clips resile to their first position when they are disengaged from the drainage tube, thereby returning the distal head to said original diameter.

16. The kit of claim 15, wherein said original diameter of the distal head is less than the smallest diameter of said drainage tube, allowing said drainage tube introducer to pass through said drainage tube.

17. The kit of claim 10, wherein said safety needle assembly further includes a first connector and said flexible sheath comprises a second connector, said first and second connectors being to mechanically couple said safety needle to said flexible sheath.

18. The kit of claim 10, further comprising a tension adjustment system for adjusting the force applied to the inner stylet by a biasing structure.

19. The kit of claim 18, wherein said biasing structure is a spring and said tension adjustment system includes multiple discrete tension settings for changing the amount of force applied by said spring to said inner stylet.

* * * * *